US010413517B2

(12) United States Patent
Haldar et al.

(10) Patent No.: US 10,413,517 B2
(45) Date of Patent: Sep. 17, 2019

(54) COMPOSITION AND METHOD FOR THE TREATMENT OF NEUROLOGICAL DISEASES AND CEREBRAL INJURY

(71) Applicant: UNIVERSITY OF NOTRE DAME DU LAC, Notre Dame, IN (US)

(72) Inventors: Kasturi Haldar, Chicago, IL (US); Md. Suhail Alam, Mishawaka, IN (US)

(73) Assignee: UNIVERSITY OF NOTRE DAME DU LAC, Notre Dame, IN (US)

( * ) Notice: Subject to any disclaimer, the term of this patent is extended or adjusted under 35 U.S.C. 154(b) by 102 days.

(21) Appl. No.: 14/737,473

(22) Filed: Jun. 11, 2015

(65) Prior Publication Data

US 2015/0359762 A1  Dec. 17, 2015

Related U.S. Application Data

(60) Provisional application No. 62/011,553, filed on Jun. 12, 2014.

(51) Int. Cl.

| | |
|---|---|
| *A61K 31/167* | (2006.01) |
| *A61K 31/724* | (2006.01) |
| *A61K 47/40* | (2006.01) |
| *A61K 47/10* | (2017.01) |
| *A61K 31/765* | (2006.01) |
| *A61K 9/00* | (2006.01) |

(52) U.S. Cl.
CPC .......... *A61K 31/167* (2013.01); *A61K 31/724* (2013.01); *A61K 31/765* (2013.01); *A61K 47/10* (2013.01); *A61K 47/40* (2013.01); *A61K 9/0019* (2013.01)

(58) Field of Classification Search
None
See application file for complete search history.

(56) References Cited

U.S. PATENT DOCUMENTS

| | | | | |
|---|---|---|---|---|
| 5,770,606 | A * | 6/1998 | El-Rashidy | A61K 9/0056 514/284 |
| 2009/0012148 | A1 | 1/2009 | Maxfield et al. | |
| 2009/0131265 | A1 | 5/2009 | Zhang | |
| 2011/0071109 | A1 | 3/2011 | Weist et al. | |
| 2011/0195873 | A1 | 8/2011 | Selinfreund et al. | |
| 2011/0237832 | A1 | 9/2011 | Helquist et al. | |
| 2017/0044590 | A1 | 2/2017 | Haldar et al. | |

FOREIGN PATENT DOCUMENTS

| | | |
|---|---|---|
| WO | WO2006120456 | 11/2006 |
| WO | WO2010138802 | 2/2010 |
| WO | WO2014022841 | 2/2014 |
| WO | WO2015042326 | 3/2015 |

OTHER PUBLICATIONS

Cai et al., "Solubilization of vorinostat by cyclodextrins", J. Clin. Pharm. Ther., 2009, vol. 34, pp. 1-6.*
Einsiedel et al., Leukemia, 2006, vol. 20, pp. 1435-1436.*
Hockly et al., PNAS, 2003, vol. 100, No. 4, pp. 2041-2046 (Year: 2003).*
Oct. 8, 2015, International Search Report issued in application PCT/US2015/035438.
Sep. 15, 2015, Written Opinion of the International Search authority issued in PCT/US2015/035438.
Mohamed, E.A., et. al., "Vorinostat with sustained exposure and high solubility in poly (ethylene glycol)-b-poly (DL-lactic acid) micelle naoncarriers: characterization and effects on pharmacokinetics in rat serum and urine.", J Pharm Sci., 2012, vol. 101 No. 10 pp. 3787-3798.
Chang, R.K. et. al., "Effect of hydroxypropyl beta-cyclodextrin on drug solubility in water-propylene glycol mixtures." Drug Dev Ind Pharm., Mar. 2004; vol. 30, No. 3, pp. 297-302.
Cheoljin, Kim et al., "Synergistic induction of apoptosis in brain cancer cells by targeted Co delivery of siRNA and anti-cancer drugs." Mol. Pharm., Oct. 3, 1961; 8(5):1955-1961. Doi:10.1021/mp100460h, pp. 1-13.
Amin, J. et al., "A cyclodextrin-capped histone deacetylase inhibitor. ", Bioorg Med Chem Lett., Jun. 1, 2013; 23(11):3346-3348.
Apr. 22, 2017, Third Party Observation as submitted in application PCT/US2014/056417.
Abi-Mosleh, Lina; "Cyclodextrin overcomes deficient lysosome-to-endoplasmic reticulum transport of cholesterol in Niemann-Pick type C cells", PNAS, Nov. 17, 2009, 19316-21, vol. 106, No. 46.
Alam, Md. Suhail, "Genomic Expression Analyses Reveal Lysosomal, Innate Immunity Proteins, as Disease Correlates in Murine Modesl of a Lysosomal Storage Disorder", PLOS One, 7(10) Oct. 2012.
Alam, Md. Suhail, "Plasma Signature of Neurological Disease in Monogenetic Disorder Niemann-Pick Type C", Journal of Biological Chemistry vol. 289, No. 12, Mar. 21, 2014, 8051-8066.
Booth, David R.,"Instability, unfolding and aggregation of human lysozyme variants underlying amyloid fibrillogenesis", Nature, vol. 385127, Feb. 1997, 787-793.
Collins, Christopher J., "Synthesis, Characterization, and Evaluation of Pluronic-Based β-Cyclodextrin Polyrotaxanes for Mobilization of Accumulated Cholesterol from Niemann-Pic Type C Fibroblasts", ACS Publications, Biochemistry, Apr. 5, 2013, 52(19) pp. 3242-3253.
Davidson, Cristin D., Chronic Cyclodextrin Treatment of Murine Niemann-Pick C Disease Ameliorates Neuronal Cholestrol and Glycosphingolipid Storage and Disease Progression, Sep. 11, 2009, PloS One vol. 4, Issue 9.
Hockey, Emma., "Suberoylanilide hydroxamic acid, a histone deacetylase inhibitor, ameliorates motor deficits in a mouse model Huntington's disease", PNAS, Feb. 18, 2003, vol. 100, No. 4, 2041-2046, www.pnas.org/cgi/doi/10.1073/pnas.0437870100.
Mar. 20, 2015, International Search Report issued in application WO2015/042326.
Koob, Andrew., "Intravenous Polyethylene Glycol Inhibits the Loss of Cerebral Cells after Brain Injury", 2005, Journal of Neurotrauma, vol. 22 No. 10, 1092-1111.
Liu, Benny., "Genetic variations and treatments that affect the lifespan of the NPC1 mouse", Dec. 12, 2007, Journal of Lipid Research vol. 49, pp. 663-669.

(Continued)

*Primary Examiner* — Jeffrey S Lundgren
*Assistant Examiner* — Stephanie K Springer
(74) *Attorney, Agent, or Firm* — Law Office of John K. Pike, PLLC

(57) ABSTRACT

Methods and compositions which include or include the administration of a hydrophobic drug, prodrug thereof, salt thereof, isoform thereof, or a combination thereof; cyclodextrin, prodrug thereof, salt thereof, or a combination thereof; polyethylene glycol, propylene glycol, or combination thereof; and optionally, a pharmaceutically acceptable carrier.

24 Claims, 9 Drawing Sheets

(56) References Cited

OTHER PUBLICATIONS

Liu, Benny., "Reversal of defective lysosomal transport in NPC disease ameliorates liver dysfunction and neurodegenration in the npc 1$^{-/-}$ mouse", Feb. 17, 2009, PNAS, vol. 106, No. 7, pp. 2377-2382 www.pnas.org/cgi/doi/10.1073/pnas.0810895106.

Liu-Snyder, Peishan, "Neuroprotection from secondary injury by polythylene gylcol requires its internalization," 2007, The Journal of Experimental Biology vol. 210, pp. 1455-1462.

Liu, Benny.,"Cyclodextrin overcomes the transport defect in nearly every organ of NPC1 mice leading to excretion of sequestered cholesterol as bile acid", 2010, Journal of Lipid Research vol. 51 pp. 933-944.

Maes, Michael,"Evidence for inflammation and activation of cell-mediated immunity in Myalgic Encephalomyelitis/Chronic Fatigue Syndrome (ME/CFS): Increased interleukin-1, tumor necrosis factor-α, PMN-elastase, lysozyme and neopterin", Oct. 4, 2011, Journal of Affective Disorders, vol. 136, pp. 933-939.

Mielcarek, Michal, "SAHA Decreases HDAC 2 and 4 Levels in Vivo and Improves Molecular Phenotypes in the R6/2 Mouse Model of Huntington's Disease", Nov. 2011, PloS One, vol. 6, Issue 11.

Pipalia, Nina H., "Histone deacetylase inhibitor treatment dramatically reduces cholesterol accumulation in Niemann-Pic type C1 mutant human fibroblasts", Apr. 5, 2011, PNAS, vol. 108, No. 14. 5620-5625.

Rosenbaum, Anton I., "Endocytosis of beta-cyclodextrins is responsible for cholesterol reduction in Niemann-Pick type C mutant cells", Mar. 23, 2010, PNAS, vol. 107, No. 12 pp. 5477-5482.

Vina, Jose, Why Women Have More Alzheimer's Disease Than Men: Gender and Mitochondrial Toxicity of Amyloid-β Peptide, 2010, Journal of Alzheimer's Disease vol. 20, S527-533.

Wehrmann, Zachary T., "Quantatitive Comparison of the Efficacy of Various Compounds in Lowering Intracellular Cholesterol Levels in Niemann-Pick Type C Fibroblasts", Oct. 2012, PloS One, vol. 7, Issue 10.

Mar. 20, 2015, Written Opinion issued for application PCT/US14/56417.

Dec. 15, 2016, International Preliminary Report on Patentability issued for application PCT/US2015/035438.

Alam, Md. Suhail, "Chronic administration of an HDAC inhibitor treats both neurological and systemic Niemann-Pick type C disease in a mouse model", Sci. Transl. Med., Feb. 17, 2016, 1-12, with Supplementary Materials, vol. 8, Issue 326, AAAS.

\* cited by examiner

Figure 6

COMPOSITION AND METHOD FOR THE TREATMENT OF NEUROLOGICAL DISEASES AND CEREBRAL INJURY

RELATED APPLICATIONS

This application claims priority to U.S. Provisional Application No. 62/011,553, filed 12 Jun. 2014, the entire contents of which being hereby incorporated by reference.

FIELD OF THE INVENTION

This application relates to compositions and methods for treating neurological and systemic diseases, proteostatic/lysosomal disorders, and the like. In particular, the application relates to compositions and methods suitable for histone deacetlylation inhibition therapy in treating Niemann-Pick Type C disease.

BACKGROUND

Histone deacetylase inhibitors (HDACi) are an important class of emerging therapeutics, approved for three rare cancers. HDACi's elicit complex cellular responses by blocking HDAC enzymes to promote acetylation of both histones and non-histone proteins. In genetic disorders, HDACi-induced histone modification can result in increased or decreased transcriptional expression of mutated gene(s) of interest but also confer indirect benefits through non-histone proteins (such as transcription factors and heat shock proteins) that modulate chaperone and proteostatic networks. Because of their broad effects on transcription, maximizing HDACi efficacy while limiting the dose is a major challenge in HDACi therapy. In developing and validating a therapeutic strategy that lowers HDACi dosage but also treats both systemic and cerebral disease, the latter presents additional challenges because it requires effective HDACi penetration across the blood brain barrier while also allowing brain HDAC function and in particular, Purkinje cell restoration, which requires HDAC3.

Niemann-Pick Type C disease (NPC) is an autosomal recessive neurodegenerative disease caused by defect in either Npc1 or Npc2 genes. 95% of NPC cases are due to defect in Npc1. The physiological function of both Npc1 and Npc2 are in the transport of cellular cholesterol. Cells with defects in these genes accumulate cholesterol primarily in late endosomal lysosomal system because of a block in cholesterol transport from the lysosome to the ER. Insertion of a point mutation in Npc1 gene that blocks cholesterol transport in cells confers neurodegenerative disease in a mouse model, providing definitive molecular evidence that NPC1 protein function is critical for disease. In NPC patients, progressive neurodegeneration is a hallmark of the NPC disease. Disease progression can be heterogeneous, and neurodegenerative decline may span one to two decades, but once initiated, leads to fatal outcomes. In early onset, splenomegaly and hepatomegaly are common presenting symptoms followed by neurocognitive and neuromuscular degeneration.

At present, the only available treatment for NPC is miglustat, an iminosugar marketed under the trade name, Zavesca™. It was developed to treat type 1 Gaucher's disease, another lysosomal disorder that arises from accumulation of glycosphingolipids. Miglustat acts as a substrate reduction therapy to decrease sphingolipids. Zavesca™ is approved for NPC treatment in Europe, Canada and Japan but was denied FDA approval because of insufficient data. Zavesca™ is therefore prescribed off-label in the U.S. It confers mild improvement in clinical neurological symptoms but fails to prevent disease progression.

2-Hydroxypropyl-β-cyclodextrin (HPBCD) is under trial as an emerging therapy. HPBCD chelates cholesterol and has therefore been proposed as a potential therapy for NPC, but it does not cross the blood brain barrier (BBB).

Generally, systemic drug delivery primarily benefits the liver and other organ systems of the body cavity, while direct drug delivery into the central nervous system (CNS) is needed for substantial neurological improvement. Direct CNS delivery inheres several disadvantages, however. It increases the procedural risk in lifelong therapies, is associated with hearing loss, and provides little or no benefit for systemic disease. The present inventors have found that there is a need for a simplified therapeutic approach to integrate the treatment of both cerebral and systemic defects in challenging genetic diseases such as NPC.

BRIEF DESCRIPTION OF THE SEVERAL EMBODIMENTS

In some embodiments, disclosed herein is a therapeutic strategy based on, inter alia, the development and validation of a murine model of a fatal cerebellar disorder Niemann-Pick Type C (NPC) disease with both cerebral and systemic defects, which closely mimics human disease.

In one embodiment, a method is provided for treating or preventing a disease or injury, comprising administering to a subject a composition, comprising:
  a hydrophobic drug, prodrug thereof, salt thereof, isoform thereof, or a combination thereof;
  cyclodextrin, prodrug thereof, salt thereof, or a combination thereof;
  polyethylene glycol, propylene glycol, or combination thereof; and
  optionally, a pharmaceutically acceptable carrier.

In another embodiment, a pharmaceutical composition is provided, comprising:
  a hydrophobic drug, prodrug thereof, salt thereof, isoform thereof, or a combination thereof;
  cyclodextrin, prodrug thereof, salt thereof, or a combination thereof;
  polyethylene glycol, propylene glycol, or combination thereof; and
  optionally, a pharmaceutically acceptable carrier.

In another embodiment, a pharmaceutical composition is provided, comprising:
  a hydrophobic drug, prodrug thereof, salt thereof, isoform thereof, or a combination thereof;
  cyclodextrin, prodrug thereof, salt thereof, or a combination thereof;
  polyethylene glycol, propylene glycol, or combination thereof; and
  optionally, a pharmaceutically acceptable carrier;
  wherein the hydrophobic drug is present in an administration amount of 0.1-500 mg/kg; and
  wherein cyclodextrin is present in an administration amount of 1000-40,000 mg/kg.

Although HDACi's are of significant interest as drugs, the major drawback to their use is the intrinsic toxicity associated with blocking nuclear targets that influence a large number of cellular pathways such as apoptosis, cell-cycle arrest, necrosis, autophagy and differentiation (to name just a few), and the like. In the context of neurodegeneration, recent studies show that HDAC3 is needed for Purkinje cell function, which is compromised in a wide range of cerebellar disorders. This has raised the issue about whether HDACi can be used to treat neurodegenerative disease, especially long-term treatments that are often required to substantially improve survival and neurobehavioral symptoms. This also holds for inhibitors designed to be specific for a given HDAC, since even a single HDAC can regulate hundreds of genes (and hence the value of synthesizing selective HDACi has been debated). Our data show that a pan HDACi, e.g., vorinostat, through a new formulation that improves its access to the brain, and coupled with a significant rest period, may indeed restore Purkinje cells and neurites in the cerebellum, and delay loss of gait/ambulation/swallowing, which are major disease domains of NPC. Short periods of HDAC inhibition by drugs is far less severe than an HDAC knockout Therefore although HDACs may be essential, effective, intermittent reduction in the brain has potential to yield, long term therapeutic value.

Vorinostat received FDA exemption for an exploratory Phase I study for NPC, which is currently accruing patients 18 years and older (https://clinicaltrials.gov/ct2/show/NCT02124083). This was in the absence of information on the efficacy of vorinostat (or other HDACi's) in animal models and their potential for treating neurological disease (in either models or patients), especially in balance with the caveats of the effects of HDACi on cerebellar function. Our data suggest vorinostat, if used alone, does not penetrate the mouse brain sufficiently to either directly stimulate NPC1 transcription and therefore protein expression in the brain or indirectly enhance NPC1 protein and Purkinje cell function in the cerebellum. Moreover, stimulation of acetylation activity in the brain requires co-administration in a formulation rather than oral administration of the drug, since a major component of complex formation HPBCD does not cross the gastrointestinal tract barrier. This heightens the importance for evidence-based animal studies of HDACi to guide treatments for human disease.

As indicated above, HPBCD injected into the CNS is also being evaluated as a therapy for NPC. Notably CNS delivery is associated with higher risk. In Phase I studies, Ommaya reservoirs implanted in the brain to directly deliver drug, were discontinued (http://www.nnpdf.org/cyclodextrin.html) and replaced with lumbar puncture (making it difficult to estimate the concentration of drug that will reach the brain). CNS delivery of HPBCD is associated with hearing loss and does not treat systemic disease, suggesting that in the long term, this strategy may limit comprehensive treatment of NPC. In contrast, and surprisingly, the composition described herein, sometimes referred to for convenience as TCF ("triple combination formulation") treats both neurological as well as systemic disease but avoids CNS delivery, which desirably reduces procedural risk and likely vastly expands the potential for treating patients worldwide and possibly outside of tertiary care centers.

We show that HDACi in the TCF may protect through increased NPC1 level by a direct increase of transcript and protein. Indirect mechanisms (such as increased expression of heat shock proteins and chaperone that stabilize NPC1 protein without increasing Npc1 transcript) may also play a role. In this regard HDACi in TCF may have higher restorative efficacy in treating neurological disease than chaperone therapies alone. With respect to the TCF, HPBCD is GRAS and no adverse effects have been reported so far about their use in limited number of NPC patients. PEG is also well tolerated. Our current dose, in some embodiments, of vorinostat of 150 mg/m$^2$ is substantially below the daily adult dose and frequency (6-900 mg/m$^2$ daily for 5 to 3 days for 21 days for hematological and solid tumors). In some embodiments, our vorinostat dose in TCF is within the weekly pediatric dose but exceeds the daily pediatric dose of 99 mg/m$^2$ (given iv daily for 28 days in cancer treatments). It is considered that dose modulations may be required for pediatric treatment. But in some embodiments, these are within 1.5 fold and may be accommodated by two consecutive days of half dose TCF administration followed by a suitable rest period. Different routes of treatment may also influence dose, but it is expected that the TCF will be applicable for treatment of both adult and pediatric disease.

In some embodiments, the formulation of the TCF was designed to be optimal for NPC treatment. However, it can be easily extended to other proteostatic/lysosomal disorders with or without neurological deficit and accompanying lipid accumulation and protein aggregation in cells and organs. Intraperitoneal HPBCD alone has been shown to be beneficial in a murine model of Alzheimer's disease. Although the mechanistic basis by which intraperitoneal HPBCD improves neurological disease remains unknown, it is reasonable to expect that the TCF that stimulates functional HDACi activity in the brain could provide significant treatment value for Alzheimer's. Other neurological diseases like Parkinson's, where cerebellar functions are compromised may also benefit from the TCF. Finally since it increases the plasma exposure of the vorinostat, the TCF and formulations derived from it could be applied to lower the dose of HDACi of the hydroxamate family (to which vorinostat and panobinostat which recently received FDA approval, belong). Since injecting twice as much vorinostat (FIG. 1) showed none of the benefits of 2-3 fold increase in vorinostat plasma exposure through TCF (FIG. 2-4), it is likely that formulation renders the HDACi in a state of improved tissue penetration, which is important since HDACi dose reduction remains a major challenge in disease (including tumor) therapy.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from the description.

DESCRIPTION OF THE DRAWINGS

The accompanying drawings form part of the present specification and are included to further demonstrate certain embodiments, which are not intended to be limiting, of the present invention. The invention may be better understood by reference to one or more of these drawings in combination with the description of the several embodiments presented herein.

FIG. 6 presents one embodiment of a proposed model for TCF in treating cerebral and systemic disease.

DETAILED DESCRIPTION OF THE SEVERAL EMBODIMENTS

Figure 1:
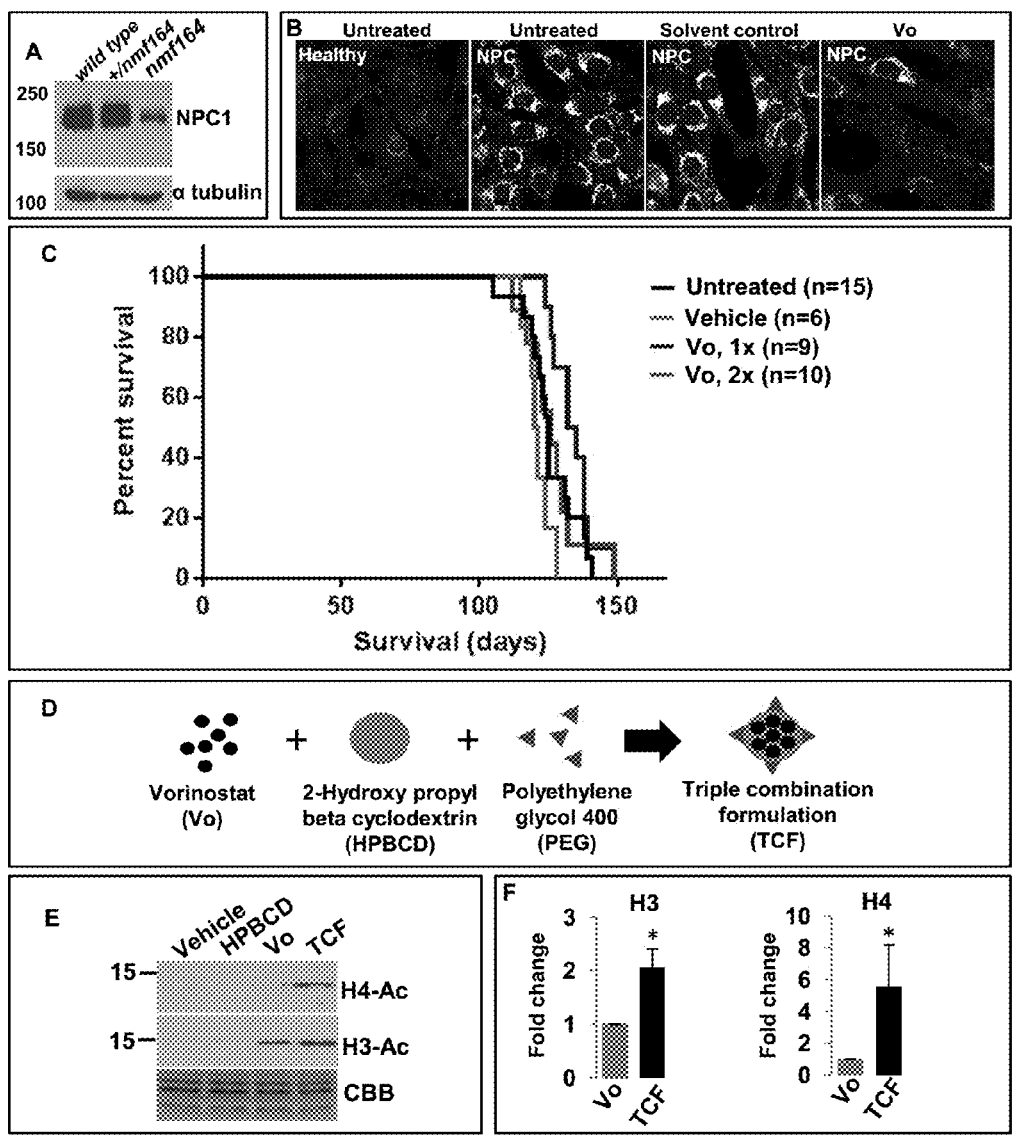
FIG. 1 shows analyses of comparative composition and an exemplary embodiment in Npc1$^{nmf164}$ mice.

Compositions and methods are disclosed herein, which provide several advantages. One advantage relates to significantly improved brain protein acetylation and preservation of neurites and Purkinje cells, broadly delayed symptoms of neurodegeneration and extended mouse life span from four to almost nine months. Another advantage relates to increased plasma concentration of an HDAC inhibitor. Another advantage relates to increased plasma concentration of Npc1 transcript levels in both the liver, which is an index of systemic expression, and the brain. Another advantage relates to increased levels of NPC1 protein in preserved cerebellar Purkinje cells. Another advantage relates to improved HDACi access across the blood brain barrier and significant attendant benefit against cerebral disease as well as cerebellar Purkinje cells and neurites. Another advantage relates to improved dose efficacy, which is a major challenge in HDACi therapy. Another advantage relates to improved therapeutic treatments for both cerebral and systemic disease in Niemann Pick Type C and other challenging disorders.

The hydrophobic drug is not particularly limiting, and it may be in any form. Non-limiting examples of the drug form include the free compound, salt thereof, prodrug thereof, isoform thereof, or any combination thereof.

In some embodiments, the hydrophobic drug is an HDAC inhibitor, or a combination of two or more HDAC inhibitors.

In some embodiments, the HDACi is a Class I, Class IIa, Class IIb, or Class IV HDAC inhibitor, or a combination thereof.

In some embodiments, the HDACi is a Class I HDAC inhibitor of the type HDAC1, HDAC2, HDAC3, or HDAC8, or a combination thereof.

In some embodiments, the HDACi is a Class IIa HDAC inhibitor of the type HDAC4, HDAC5, HDAC7, or HDAC9, or a combination thereof.

In some embodiments, the HDACi is a Class IIb HDAC inhibitor of the type HDAC6 or HDAC10, or a combination thereof.

In some embodiments, the HDACi is a Class IV HDAC inhibitor of the type HDAC11.

In some embodiments, the HDACi is a Class I or Class II HDAC inhibitor, or a combination thereof.

Non-limiting examples of HDAC inhibitors include hydroxamic acids, aliphatic acids, hydroxamates, benzamides, thiophene benzamide, butyrates, sodium butyrate, phenylbutyrate, cyclic tetrapeptide, trapoxin B, depsipeptide, cyclic peptide, electrophilic ketones, dacinostat/LAQ-824, NVP-LAQ824, givinostat/ITF-2357, bufexamac, pyroxamide, sulforaphane, trichostatin A (TSA) and analogs thereof, miglustat/OGT-918, SAHA/vorinostat/MK-0683/Zolinza, entinostat/MS-275, panobinostat/LBH-589, droxinostat/CMH, quisinostat/JNJ-26481585, PCI-24781/CRA-024781, romidepsin/FK228/FR901228/NSC 630176/depsipeptide, valproic acid, PCI-34051, CI-994/tacedinaline, M-344, rocilinostat/ACY-1215, apicidin, R-306465, mocetinostat/MGCD-0103, belinostat/PXD-101, chidamide/CS-055, abexinostat/PCI-24781, SB-939, resminostat/4SC-201, kevetrin, CUDC-101, AR-42, CHR-2845, CHR-3996, 4SC-202, CG-200745, ACY-1215, ME-344, RGFP-136, CBHA, AN-9, or any combination thereof.

In some embodiments, the HDACi is a hydroxamate, hydroxamic acid, or combination thereof.

In some embodiments, the HDACi is a hydroxamate, hydroxamic acid, vorinostat (SAHA), belinostat/PXD101, LAQ824, panobinostat/LBH-589, givinostat/ITF2357, pyroxamide, trichostatin A, CBHA, or any combination thereof.

In some embodiments, the HDACi is vorinostat.

Mixtures of two or more HDACi's are possible.

The dosage amount of the hydrophobic drug is not particularly limiting. In some embodiments, the hydrophobic drug may be administered in an amount ranging from 0.1-500 mg/kg. This range includes all values and subranges therebetween, including 0.1, 0.5, 1, 5, 10, 15, 20, 25, 30, 35, 40, 45, 50, 55, 60, 65, 70, 75, 80, 85, 90, 95, 100, 150, 200, 250, 300, 350, 400, 450, 500 mg/kg, or any combination thereof. In some embodiments, the dosage amount is based on a 50 mg/kg murine dose, and may be scaled for human treatment, as is known. For example, a 50 mg/kg murine dose may scale to 150 mg/m$^2$ in children. Such scaling is well within the skill of the artisan and may be suitably applied to any dosage for any compound or compounds herein.

The cyclodextrin is not particularly limiting. Some non-limiting examples of cyclodextrin include one or more of hydroxypropyl-β-cyclodextrin, 2-hydroxypropyl-β-cyclodextrin, dimethyl-β-cyclodextrin, hydroxypropyl-α-cyclodextrin, hydropropyl-γ-cyclodextrin, or any combination thereof.

In some embodiments, the cyclodextrin is β-cyclodextrin.

In some embodiments, the cyclodextrin is hydroxypropyl-β-cyclodextrin.

In some embodiments, the cyclodextrin is 2-hydroxypropyl-β-cyclodextrin.

The cyclodextrin may have any average molecular weight ranging, for example from about 970 to 6,000 Da depending, for example, on the type of cyclodextrin (α, β, or γ) and whether it is crosslinked or uncrosslinked, substituted or unsubstituted, the degree of substitution, and the like, as is known in the art. Accordingly, the cyclodextrin may be crosslinked or uncrosslinked, substituted or unsubstituted, or any combination thereof.

Referring to the molecular weight, the aforementioned range includes all values and subranges therebetween, including about 970, 972, 980, 990, 1000, 1010, 1030, 1050, 1070, 1090, 1100, 1120, 1140, 1160, 1180, 1200, 1250, 1300, 1350, 1370, 1380, 1390, 1395, 1400, 1410, 1420, 1430, 1440, 1460, 1480, 1500, 1600, 1800, 2000, 2500, 3000, 3500, 4000, 5000, 6000 Da, or combination thereof. In some embodiments, the cyclodextrin is 2-hydroxypropyl-β-cyclodextrin and may have an average molecular weight of 1396 Da. In some embodiments, the cyclodextrin is α-cyclodextrin and may have an average molecular weight of 973 Da. In some embodiments, the cyclodextrin is β-cyclodextrin and may have a molecular weight of 1135 Da. In some embodiments, the cyclodextrin is γ-cyclodextrin and may have a molecular weight of 1297 Da.

If substituted, the cyclodextrin may have a degree of substitution, or average number of substituents per glucopyranose unit, ranging from 0.5 to 3. This range includes any value or subrange therebetween, including 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.2, 2.4, 2.5, 2.6, 2.7, 2.8, 2.9, 3, or any combination thereof.

The cyclodextrin is preferably water soluble. The cyclodextrin may have a water solubility at 25° C. from about 10 mg/ml and higher. This range includes all values and subranges therebetween, including about 10, 20, 40, 60, 100, 200, 300, 400, 500, 600 mg/ml and higher.

Mixtures of different cyclodextrins are possible.

In some embodiments, the cyclodextrin is 2-hydroxypropyl-β-cyclodextrin, having an average molecular weight of 1396 Da and an average degree of substitution of 0.67 hydroxypropyl groups per glucopyanose unit.

The dosage amount of the cyclodextrin is not particularly limiting. In some embodiments, the cyclodextrin may be administered in an amount ranging from 1000-40,000 mg/kg. This range includes all values and subranges therebetween, including 1000, 1200, 1400, 1600, 1800, 2000, 2100, 2200, 2300, 2400, 2500, 2600, 2700, 2800, 2900, 3000, 3500, 4000, 5000, 6000, 7000, 8000, 9000, 10,000, 20,000, 30,000, 40,000 mg/kg, or any combination thereof. In some embodiments, the dosage amount is based on a 2000 mg/kg murine dose, and may be scaled for human treatment, as is known.

In some embodiments, it may be desirable to use derivatives of cyclodextrin, e.g., the so-called polyrotaxanes in place of the aforementioned cyclodextrins or in addition to them in the composition. Polyrotaxanes are a new class of supramolecular materials in which β-cyclodextrins are threaded along a polymer chain capped with bulky terminal moieties. Polyrotaxanes are known and have been cited in the literature as potentially useful therapeutics to combat cholesterol accumulation in the treatment of NPC. Non-limiting examples of polyrotaxanes include 2-hydroxypropyl-β-cyclodextrin/plurionic-based polyrotaxanes, biocleavable plurionic/β-cyclodextrin polyrotaxanes, and the like. These and other examples of polyrotaxanes are disclosed in Tamura, A. & N. Yui, *Scientific Reports* 4: 4356 (2014) and Mondjinou, Y. A., et al., *Biomacromolecules* 14: 4189-4197 (2013), incorporated herein by reference.

The polyethylene glycol and propylene glycol are not particularly limiting. In some embodiments, polyethylene glycol is used.

The molecular weight of the polyethylene glycol or polypropylene glycol is not particularly limiting. In some embodiments, the average molecular weight may range from 100 to 6000 Da. This range includes all values and subranges therebetween, including 100, 200, 300, 400, 500, 600, 700, 800, 900, 1000, 1200, 1400, 1600, 1800, 2000, 2100, 2200, 2300, 2400, 2500, 2600, 2700, 2800, 2900, 3000, 3500, 4000, 5000, 6000 Da, or any combination thereof.

In some embodiments, polyethylene glycol is used, and the average molecular weight may range from 100 to 6000 Da. This range includes all values and subranges therebetween, including 100, 200, 300, 400, 500, 600, 700, 800, 900, 1000, 1200, 1400, 1600, 1800, 2000, 2100, 2200, 2300, 2400, 2500, 2600, 2700, 2800, 2900, 3000, 3500, 4000, 5000, 6000 Da, or any combination thereof.

In some embodiments, polyethylene glycol having an average molecular weight of 100-1000 Da is used. In some embodiments, polyethylene glycol having an average molecular weight of 200-600 is used. In some embodiments, polyethylene glycol having an average molecular weight of 400 is used.

Mixtures of polyethylene glycols having different molecular weights are possible.

The amount of polyethylene glycol is not particularly limiting. In some embodiments, the amount of polyethylene glycol may suitably range from 1 to 80% of the composition by weight. This range includes all values and subranges therebetween, including 1, 2, 3, 4, 5, 6, 7, 8, 9, 10, 15, 20, 25, 30, 35, 40, 45, 50, 55, 60, 65, 70, 75, 80%, or any combination thereof, based on the weight of the composition.

The relative amounts of hydrophobic drug:cyclodextrin:polyethylene glycol or propylene glycol are not particularly limiting. In some embodiments, the hydrophobic drug:cyclodextrin:polyethylene glycol or propylene glycol molar ratio may be 1-100:1-1000:1-1000. Each of these ranges independently includes all values and subranges therebetween. For example, the 1-100 range given for the hydrophobic drug independently includes all values and subranges therebetween, including 1, 2, 3, 4, 5, 6, 7, 8, 9, 10, 15, 20, 25, 30, 35, 40, 45, 50, 55, 60, 65, 70, 75, 80, 85, 90, 95, 100, or any combination thereof. Similarly, the 1-1000 range given for the cyclodextrin independently includes all values and subranges therebetween, including 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or any combination thereof. Likewise, the 1-1000 range given for the polyethylene glycol or polypropylene glycol independently includes all values and subranges therebetween, including 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or any combination thereof.

In some embodiments, the hydrophobic drug:cyclodextrin:polyethylene glycol or propylene glycol molar ratio may be 1-100:1-100:1-1000. Each of these ranges independently includes all values and subranges therebetween. For example, the 1-100 range given for the hydrophobic drug independently includes all values and subranges therebetween, including 1, 2, 3, 4, 5, 6, 7, 8, 9, 10, 15, 20, 25, 30, 35, 40, 45, 50, 55, 60, 65, 70, 75, 80, 85, 90, 95, 100, or any combination thereof. Similarly, the 1-100 range given for the cyclodextrin independently includes all values and subranges therebetween, including 1, 2, 3, 4, 5, 6, 7, 8, 9, 10, 15, 20, 25, 30, 35, 40, 45, 50, 55, 60, 65, 70, 75, 80, 85, 90, 95, 100, or any combination thereof. Likewise, the 1-1000 range given for the polyethylene glycol or polypropylene glycol independently includes all values and subranges therebetween, including 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or any combination thereof.

In some embodiments, the composition has a hydrophobic drug:cyclodextrin:polyethylene glycol molar ratio of 1-10:1-1000:1-1000. In some embodiments, the composition has a hydrophobic drug:cyclodextrin:polyethylene glycol molar ratio of 1-10:1-100:1-1000.

In some embodiments, the composition has a hydrophobic drug:cyclodextrin:polyethylene glycol molar ratio of 1:1-100:1-500. In some embodiments, the composition has a hydrophobic drug:cyclodextrin:polyethylene glycol molar ratio of 1:1-10:1-100.

In some embodiments, the composition has a hydrophobic drug:cyclodextrin:polyethylene glycol molar ratio of 1:5-

100:10-100. In some embodiments, the composition has a hydrophobic drug:cyclodextrin:polyethylene glycol molar ratio of 1:5-10:10-100.

In some embodiments, the composition includes HDACi, cyclodextrin, and polyethylene glycol in a HDACi:cyclodextrin:polyethylene glycol molar ratio of 1-100:1-1000:1-1000. In some embodiments, the composition includes HDACi, cyclodextrin, and polyethylene glycol in a HDACi:cyclodextrin:polyethylene glycol molar ratio of 1-100:1-100:1-1000.

In some embodiments, the composition includes HDACi, 2-hydroxypropyl-β-cyclodextrin, and polyethylene glycol 400 in a HDACi:2-hydroxypropyl-β-cyclodextrin:polyethylene glycol 400 molar ratio of 1-100:1-1000:1-1000. In some embodiments, the composition includes HDACi, 2-hydroxypropyl-β-cyclodextrin, and polyethylene glycol 400 in a HDACi:2-hydroxypropyl-β-cyclodextrin:polyethylene glycol 400 molar ratio of 1-100:1-100:1-1000.

In some embodiments, the composition includes vorinostat, 2-hydroxypropyl-β-cyclodextrin, and polyethylene glycol 400 in a vorinostat:2-hydroxypropyl-β-cyclodextrin:polyethylene glycol 400 molar ratio of 1-100:1-1000:1-1000. In some embodiments, the composition includes vorinostat, 2-hydroxypropyl-β-cyclodextrin, and polyethylene glycol 400 in a vorinostat:2-hydroxypropyl-β-cyclodextrin:polyethylene glycol 400 molar ratio of 1-100:1-100:1-1000.

The molar ratio of hydrophobic drug:cyclodextrin is not particularly limiting, and may suitably range from 0.001 to 100. This range includes all values and subranges therebetween, including 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or any combination thereof.

Similarly, the molar ratio of hydrophobic drug:polyethylene glycol is not particularly limiting, and may suitably range from 0.001 to 100. This range includes all values and subranges therebetween, including 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or any combination thereof.

In some embodiments, the composition has a hydrophobic drug:cyclodextrin molar ratio of less than 0.2, ≤0.13, less than 0.13, 0.001 to less than 0.2, 0.001 to ≤0.13, 0.001 to less than 0.13, 0.01 to 0.15, 0.01 to ≤0.13, 0.01 to less than 0.13, 0.01 to ≤0.1, 0.01 to less than 0.1, 0.01 to ≤0.065, 0.01 to less than 0.065, about 0.13, or about 0.065 as appropriate.

In some embodiments, the composition has a HDACi:cyclodextrin molar ratio of less than 0.2, ≤0.13, less than 0.13, 0.001 to less than 0.2, 0.001 to ≤0.13, 0.001 to less than 0.13, 0.01 to 0.15, 0.01 to ≤0.13, 0.01 to less than 0.13, 0.01 to ≤0.1, 0.01 to less than 0.1, 0.01 to ≤0.065, 0.01 to less than 0.065, about 0.13, or about 0.065 as appropriate.

In some embodiments, the composition has a vorinostat:2-hydroxypropyl-β-cyclodextrin molar ratio of less than 0.2, ≤0.13, less than 0.13, 0.001 to less than 0.2, 0.001 to ≤0.13, 0.001 to less than 0.13, 0.01 to 0.15, 0.01 to ≤0.13, 0.01 to less than 0.13, 0.01 to ≤0.1, 0.01 to less than 0.1, 0.01 to ≤0.065, 0.01 to less than 0.065, about 0.13, or about 0.065 as appropriate.

In some embodiments, the composition has a hydrophobic drug:polyethylene glycol or propylene glycol molar ratio of less than 1, 0.9, 0.8, 0.7, 0.6, 0.5, 0.4, 0.3, 0.2, 0.15, 0.1, 0.09, 0.08, 0.07, 0.06, 0.05, 0.04, 0.03, 0.02, 0.15, 0.01, or any combination thereof.

In some embodiments, the composition has a hydrophobic drug:polyethylene glycol molar ratio of less than 1, 0.9, 0.8, 0.7, 0.6, 0.5, 0.4, 0.3, 0.2, 0.15, 0.1, 0.09, 0.08, 0.07, 0.06, 0.05, 0.04, 0.03, 0.02, 0.15, 0.01, or any combination thereof.

In some embodiments, the composition has a HDACi:polyethylene glycol 400 molar ratio of less than 1, 0.9, 0.8, 0.7, 0.6, 0.5, 0.4, 0.3, 0.2, 0.15, 0.1, 0.09, 0.08, 0.07, 0.06, 0.05, 0.04, 0.03, 0.02, 0.15, 0.01, or any combination thereof.

In some embodiments, the composition has a vorinostat:polyethylene glycol 400 molar ratio of less than 1, 0.9, 0.8, 0.7, 0.6, 0.5, 0.4, 0.3, 0.2, 0.15, 0.1, 0.09, 0.08, 0.07, 0.06, 0.05, 0.04, 0.03, 0.02, 0.15, 0.01, or any combination thereof.

In some embodiments, the composition does not contain fibroblasts, other biological organisms, or the like.

The composition may or may not contain DMSO. In some embodiments, the composition does not contain DMSO.

The composition may be administered as a single dose, or the composition components may be administered separately. For example, in some embodiments, cyclodextrin may be administered separately from the hydrophobic drug and polyethylene glycol or polypropylene glycol. In some embodiments, the method includes administering cyclodextrin before or after administering the hydrophobic drug and polyethylene glycol or polypropylene glycol. In some embodiments, the method includes administering cyclodextrin before administering the remaining components. In some embodiments, the method includes administering the hydrophobic drug separately. Preferably, however, the composition is administered as a single admixture.

The timing of the administration is not particularly limiting. For example, administering may occur once or more than once. In some embodiments, the administering is carried out periodically or substantially periodically, for example, daily, weekly, monthly, a multiple thereof, a fraction thereof, or a combination thereof. In some embodiments, the administering is carried out daily, a multiple thereof, a fraction thereof, or a combination thereof. In some embodiments, the administering is carried out weekly, a multiple thereof, a fraction thereof, or a combination thereof. In some embodiments, the administration may occur regularly, e.g., every week throughout the duration of treatment, or it may occur irregularly, e.g., once a week for a few weeks, then twice a week or not at all for a few weeks, etc. Similarly, in some embodiments, a rest period of non-administration may occur between administrations. The rest period may occur regularly or irregularly.

The disease is not particularly limiting. Non-limiting examples of diseases include one or more of disease of the brain, cerebral injury, brain and systemic disease, brain and systemic disease for which the liver read out, neurological disease, cerebral injury, disease associated with loss or reduction of level of calbindin, neurotoxicity, Niemann-Pick disease, Niemann-Pick Type C disease, neurodegenerative disorder, TBI, autism, Alzheimer's, cutaneous T cell lymphoma, B cell lymphoma, inflammatory disorder, neuroinflammatory disorder, neuroinflammation due to lysosomal storage disorder, lysosomal storage disorder, Sezary syndrome, Gliobastoma multiforme, Myeloddysplastic syndrome, non small cell lung cancer, HIV, non-neurological disease, brain tumor, disease responsive to treatment with histone deacetylase (HDAC) inhibitor, disease involving plasma concentration of vorinostat (SAHA), disease responsive to treatment with SAHA, disease where effect of SAHA is observed in animal model, encephalopathy, epilepsy, cerebrovascular disease, disease responsive to penetration of drug through the blood-brain barrier, Parkinsons, Amyotrophic Lateral Sclerosis, activator deficiency/GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, Gaucher's disease, Gaucher disease (types I-III), GM1 gangliosidosis, I-cell disease/mucolipidosis II, infantile free sialic acid storage disease/ISSD, juvenile hexosaminidase A deficiency, Krabbe disease, metachromatic leukodystrophy, mucopolysaccharidoses disorders, pseudo-Hurler polydystrophy/mucolipidosis IIIA, MPSI Hurler syndrome, MPSI Scheie syndrome, MPS I Hurler-Scheie syndrome, MPS II Hunter syndrome, Sanfilippo syndrome, Morquio syndrome, MPS IX hyaluronidase deficiency, MPS VI Maroteaux-Lamy, MPS VII Sly syndrome, mucolipidosis I/sialidosis, multiple sulfatase deficiency, neuronal ceroid lipofuscinoses, Pompe disease, pycnodysostosis, Sandhoff disease, Schindler disease, Salla disease, Tay-Sachs, Wolman disease, advanced solid tumors, treatment-resistant multiple myeloma, chronic lymphocytic leukemia or lymphoma, advanced hematological indications, multiple myeloma, solid refractory tumors, polycythemia vera, essential thrombocythemia, myelofibrosis, acute myocardial infarction, pancreatic cancer, cervical cancer, ovarian cancer, spinal muscular atrophy, relapsed ovarian cancer, follicular lymphoma, Huntington's disease, Hodgkin lymphoma, acute myeloid leukemia, sarcoma, lymphoma, lung cancer, breast cancer, recurrent or metastatic prostate cancer, hepatocellular carcinoma, ovarian cancer spleen metastasis, or a combination thereof.

In some embodiments, the composition can be administered to a human or other mammalian patient by itself or in a pharmaceutical composition where it may be mixed with suitable carriers or excipients at doses to treat or ameliorate the disease or symptom thereof for which treatment is administered. A therapeutically effective dose may refer to that amount of the composition sufficient to treat or ameliorate the disease or symptom thereof for which treatment is administered, it being understood that such treatment or amelioration may occur at different concentrations such that a person skilled in the art could determine the required dosage of the composition in light of the teachings herein. Therapeutically effective doses may be administered alone or as adjunctive therapy in combination with other treatments. Some examples of techniques for the formulation and administration of the compositions may be found in Remington's Pharmaceutical Sciences, 18th Edition, A. R. Gennaro, Ed., Mack Publishing Co., Easton, Pa. (1990).

The route of administration is not particularly limited. Non-limiting examples of suitable routes of administration may, for example, include oral, rectal, transmucosal, buccal, intravaginal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. Furthermore, one may administer the composition in a targeted drug delivery system, for example in a liposome.

In some embodiments, the composition may be administered systemically, whereas in other embodiments the composition may be administered locally. For example, in some embodiment, systemic administration may be oral, by injection, intravenous, intra-arterial, subcutaneous, intramuscular, intrathecal, or intraperitoneal injection. Systemic administration also may include transdermal or inhalational administration.

In some embodiments, the composition may be administered locally. For example, in some embodiments, local administration may be accomplished by local injection into the body part that is particularly affected, for example by injecting or infusing the composition directly into the CNS or brain, e.g., intrathecally, or into the ocular space. In other embodiments, local administration may be accomplished by implanting a sustained-release device such as a pump or micropump, or a sustained-release implant, such as a bead or gel that contains the composition and slowly releases it into the desired area over time.

The pharmaceutical compositions and/or compounds may be manufactured in a manner that is itself known, e.g., by means of conventional mixing, dissolving, dragee-making, levitating, emulsifying, encapsulating, entrapping, or lyophilizing processes. The pharmaceutical compositions thus may be formulated in conventional manner using one or more physiologically acceptable carriers comprising excipients and auxiliaries that facilitate processing of the active compounds or composition into preparations, which can be used pharmaceutically. Proper formulation may be dependent upon the route of administration chosen. For example, a composition intended for ocular administration might include an aqueous carrier and one or more of viscosity agent, ocular buffer, pH buffer, isotonic buffer, and the like.

Any combination of one or more the compounds, salts thereof, resonance forms thereof, prodrugs, metabolites, isotopically-labeled compounds, tautomers, isomers, and/or atropisomers is possible in the composition.

For injection, the composition and/or compounds may be formulated in aqueous solutions, preferably in physiologically compatible buffers, such as Hank's solution, Ringer's solution, or physiological saline buffer. For transmucosal administration, penetrants appropriate to the barrier to be permeated may be suitably used in the formulation. Such penetrants are known in the art.

For oral administration, the composition and/or compounds can be formulated readily by combining the active compounds and/or composition with pharmaceutically acceptable carriers well known to those in the art. Such carriers enable the compounds and/or composition to be formulated as tablets, pills, dragees, capsules, liquids, gels, syrups, slurries, suspensions and the like, for oral ingestion by a patient to be treated. Pharmaceutical preparations for oral use can be obtained by combining the compound and/or composition with a solid excipient, optionally grinding the resulting mixture, and processing the mixture of granules, after adding suitable auxiliaries, if desired, to obtain tablets or dragee cores. Suitable excipients include but are not limited to fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, polyvinylpyrrolidone, and the like. If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used in some embodiments, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings if desired for identification or to characterize different combinations of active compound or composition doses.

Other non-limiting examples of pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds and/or composition may be dissolved or suspended in suitable liquids, such as fatty oils, liquid paraffin, or the like. In addition, stabilizers may be added. All formulations for oral administration should be in dosages suitable for such administration.

For buccal administration, the compositions may take the form of tablets or lozenges formulated in conventional manner.

For administration by inhalation, the compounds and/or composition may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds and/or composition may be formulated for parenteral administration by injection, e.g., by bolus injection or continuous infusion. Formulations for injection may be presented in unit dosage form, e.g., in ampoules or in multi-dose containers, optionally with an added preservative. The compositions may take such forms as suspensions, solutions or emulsions in oily or aqueous vehicles, and may contain formulatory agents such as suspending, stabilizing and/or dispersing agents.

Other pharmaceutical formulations for parenteral administration include aqueous solutions of the active compounds or composition in water-soluble form. Additionally, suspensions of the active compounds or composition may be prepared as appropriate oily injection suspensions. Non-limiting examples of suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as polyionic block (co)polymer, sodium carboxymethyl cellulose, sorbitol, or dextran. Optionally, the suspension may also contain suitable stabilizers or agents which increase the solubility of the compounds.

Alternatively, the active ingredient may be in powder form for constitution with a suitable vehicle, e.g., sterile pyrogen-free water, before use.

The compounds and/or composition may also be formulated in rectal compositions such as suppositories or retention enemas, e.g., containing conventional suppository bases such as cocoa butter or other glycerides.

The compounds and/or composition may also be formulated as a depot preparation. Such long acting formulations may be administered by implantation (for example subcutaneously or intramuscularly) or by intramuscular injection. Thus, for example, the compounds and/or composition may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may include suitable solid- or gel-phase carriers or excipients. Examples of such carriers or excipients include but are not limited to calcium carbonate, calcium phosphate, various sugars, starches, cellulose derivatives, gelatin, and pharmaceutically acceptable polymers.

In some embodiments, the compounds may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Non-limiting examples of pharmaceutically acceptable salts include sodium, potassium, lithium, calcium, magnesium, iron, zinc, hydrochloride, hydrobromide, hydroiodide, acetate, citrate, tartrate and maleate salts, and the like.

Generally, pharmaceutical compositions contain the active compound or compounds in an effective amount to achieve their intended purpose. In one embodiment, a therapeutically effective amount means an amount effective to prevent or inhibit development or progression of a disease in a subject, who is known to have or suspected of having or at risk of having the disease. Determination of the effective amounts is within the capability of those skilled in the art in light of the teachings herein.

The use of the word "a" or "an" when used in conjunction with the term "comprising" in the claims and/or the specification may mean "one," but it is also consistent with the meaning of "one or more," "at least one," and "one or more than one."

The term, "about" is used to indicate that a value includes the standard deviation of error.

The term, "or" means "and/or" unless explicitly indicated to refer to alternatives only or the alternatives are mutually exclusive, although the disclosure supports a definition that refers to only alternatives and "and/or."

The terms "embodiment" or "embodiments" may each refer to one or more of the same or different embodiments. Further, the terms "comprising," "including," "having," and the like, as used with respect to embodiments, are synonymous. The terms, "triple combination formulation" and "TCF" are used herein for convenience only, and are not intended to be limiting. Therefore, the scope of embodiments, whether referred to as triple combination formulation, TCF, or otherwise, is defined by the claims and their equivalents.

EXAMPLES

Materials and Methods
Study design
The present study, inter alia, evaluated the efficacy of Vorinostat (Vo) an HDACi for the treatment of Niemann-Pick Type C disease in a mouse model. Vo was found to be effective in reducing the intracellular cholesterol burden in in vitro grown mouse skin fibroblasts but did not have any survival benefit when administered to NPC mice. We hypothesized poor solubility, reduced plasma exposure and penetration across the Blood Brain Barrier (BBB) of Vo to be the possible reasons behind its ineffectiveness in the animals. To overcome these limitations, we used HPBCD as an excipient and made a formulation that contained Vo, HPBCD and polyethylene glycol (PEG) and named it Triple combination Formulation (TCF). The effect of TCF was evaluated using different molecular, biochemical, histological and neurobehavioral measures in NPC mice at indicated ages. For survival and neurobehavioral testing 8-10 mice were used in groups injected with drug. At least 6 mice were used in vehicle treated group. End point for survival studies were set at ≥30% weight loss. For molecular, biochemical, histological analyses at least 3-4 mice were used with at least two technical replicates in each assay. Animals were randomly assigned to treatment groups. Equal numbers of males and females were included in each group. Two independent PK experiments in mice were done each containing 5 mice in a group. The reliability and robustness of neurobehavioral scoring system was evaluated by two blinded investigators. Investigators were blinded to the drug injections while assessing the neurobehavioral functions. Determination of Vo in plasma samples were done by blinded investigators at the Metabolite Profiling Facility, Purdue University, IN, USA. Sample sizes were chosen based on previous experience or similar studies conducted by others. All data points were used in the statistical analyses.

Materials

All fine chemicals including HPBCD powder (H107) and PEG400 were obtained from Sigma (St Louis, Mo., USA), unless otherwise indicated. Vorinostat was from Selleck Chemicals (Houston, Tex., USA). DMEM and trypsin were from Life Technologies (New York, N.Y., USA). FBS was procured from ATCC. Oligonucleotides for qPCR were purchased from Invitrogen (Carlsbad, Calif., USA).

Animals

Npc1$^{nmf164}$, BALB/c strain carrying an aspartate to glycine mutation at position 1005 (D1005G) in Npc1 gene was used as NPC disease model. (Maue, R. A., et al., *Hum Mol Genet* 21: 730-750 (2012)).When animals were sick and unable to reach the food provided on the holder, regular food (2019 Teklad diet, Harlan Laboratories, Indianapolis, Ind.) was replaced with DietGel 76A (Clear $H_2O$, Portland, Me.). Studies with mice were performed with approval and authorization from the Institutional Animal Care and Use Committee of University of Notre Dame, Indiana, USA.

Preparation of Drug and Injection to Mice

Vorinostat (50 mg/Kg)—Vorinostat was first dissolved in DMSO (100 mg/ml) and then diluted with 9 volume of Polyethylene Glycol 400 (PEG). This drug solution was named as 'solution A'. Solution A was diluted with equal volume of water where the final concentration of each component was as follows; Vorinostat, 5 mg/ml; DMSO, 5% and PEG, 45%. Mice were given weekly intraperitoneal (i.p) injections starting at 21 days. Vorinostat (100 mg/Kg)—Vorinostat was first dissolved in DMSO (200 mg/ml) and then mixed with 9 volumes of PEG. Rest of the methods and injections plan were as described above. HPBCD (4000 mg/Kg)—40% HPBCD solution prepared in water. Mice were given weekly i.p injections starting at 7 days. HPBCD (2000 mg/Kg)—20% HPBCD solution prepared in water. Mice were given weekly i.p injections starting at 7 days. TCF (Vorinostat, 50 mg/Kg+HPBCD, 2000 mg/Kg, DMSO, 5%+PEG, 45%)—To prepare the formulation, the 'solution A' was first prepared as described above and equal volume of 40% HPBCD solution was slowly layered on top of it. The solution was gently mixed for 10 min at RT on rocker set at medium speed. The final concentration of each component in the formulation was as follows; Vorinsotat, 5 mg/ml; DMSO 5%; PEG, 45%; and HPBCD, 20%. Mice were given two i.p doses of HPBCD (2000 mg/Kg) at 7 and 15 days. Starting from 21 days mice were given weekly i.p injection of TCF. Vehicle control (5% DMSO and 45% PEG)—It was made by mixing 1 volume of DMSO with 9 volume of PEG and then diluted with equal volume of water.

Mice were given weekly i.p injection starting from 21 days. All drug solutions were stored at −80° C. Fresh vials of frozen stock were thawed for injection on different days. The injection volume across the treatment group was 10 ml/Kg body weight. For marker analysis mice were sacrificed at 100 days and organs were harvested. For survival studies, injections were continued until the death. Death was defined when animal was either found dead or lost ≥30% of maximum weight or unable to eat or drink even after providing DietGel 7A (Clear $H_2O$, Portland, Me.).

Quantitative PCR

Quantitative PCR (qPCR) was performed using Power SYBR Green RNA-to-$C_T$ 1-Step Kit and an ABI Prism 7500 Fast real-time PCR system (Applied Biosystems, Grand Island, USA). Gapdh (Glyceraldehyde 3-phosphate dehydrogenase) was used as an endogenous control. The relative amount of transcript was determined using comparative $C_T$ method. Untreated Npc1$^{+/-}$ served as a reference.

Organ Harvest and Immunefluorescence Assay

Mice were sacrificed by asphyxiation using $CO_2$. Harvested organs were immersed fixed in 10% neutral buffered formalin (~4% formaldehyde) for 24 hrs at RT. The organs were subsequently stored in 70% alcohol at RT until transfer to paraffin. Paraffin-embedded tissue sections (4-5 µm) were dewaxed in xylene and alcohol. Calbindin antigen retrieval was done by pre-incubating deparaffinized samples with 0.05% proteinase K (Dako, Germany) in 50 mM Tris-HCl (pH 7.5) for 8 min at RT. CTSS and NPC1 was retrieved by boiling the sections in acidic condition for 30 min. Blocking was done either with 2% goat serum (for calbindin and NPC1) or 2% rabbit serum (for cathepsin S) for 30 min at RT. Sections were incubated with anti-calbindin (1:1000, C9848, Sigma), anti-cathepsin S (20 µg/ml, M-19, Santa Cruz Biotechnology), anti-NPC1 (custom made against human NPC1 protein, 20 µg/ml) overnight at 4° C. The appropriate FITC or TRITC-conjugated secondary IgG (MP Biomedicals, Solon, Ohio, USA) antibodies were used at 1:200 dilution. Sections were subsequently washed with PBS containing DAPI (0.5 µg/ml). Vectashield (Vector laboratories) was used as mounting medium and processed for fluorescence microscopy.

Histone Acetylation

Npc1$^{nmf164}$ mice (6-7 weeks) were injected with either Vorinostat (50 mg/kg) or TCF through i.p route. Mice were sacrificed 1 hpi (1 hour post-injection) by asphyxiation using $CO_2$. After homogenization of tissue, Histones were extracted using EpiQuik Total Histone extraction kit (Epigentek, NY, USA) as per manufacturer's instructions. Antibodies to Histone H3 (Lys14) and H4 (Lys5/8/12/16) from Millipore (CA, USA) were used in western blotting.

Mouse Fibroblasts Culture and Drug Treatment

Ear pinna was cleaned with 70% alcohol and 2-3 small pieces (3×3 mm) were chopped and placed in 70% alcohol for 2 min and transferred to DMEM. Tissues were cut into small pieces and 2 ml of 0.25% trypsin were added, vigorously vortexed for 2 min and incubated at 37° C. with vortexing every 10 min. Trypsin was inactivated by adding 2 ml of culture media (DMEM+10%FBS). Cells were collected by spin (1000 rpm for 5 min), and were grown in DMEM+10% FBS in the presence penicillin (50 U/ml) and streptomycin (50 µg/ml). For treatment with vorinostat, fibroblasts (4×10$^4$) were plated in 24 well plate containing glass slide. Npc1$^{nmf164}$ fibroblasts were treated with 5 µM vorinostat for 48 hrs. Cells incubated with 0.025% DMSO served as vehicle control. Cells were fixed with 4% paraformaldehyde followed by incubation with filipin (100

μg/ml) to stain cholesterol. Slides were mounted using Vectashield (Vector laboratories) and processed for fluorescence microscopy.

Fluorescence Microscopy

Tissue sections after IFA and filipin stained fibroblasts were visualized with 40× oil-immersion objective lens (NA 1.35). Filipin stain was visualized using DAPI filter. Digital image collection were performed using an Olympus IX inverted fluorescence microscope and a Photometrix cooled CCD camera (CH350/LCCD) driven by DeltaVision software from Applied Precision (Seattle, Wash., USA). DeltaVision software (softWoRx) was used to deconvolve these images. Images are single optical sections. Images were analyzed using ImageJ software (NIH, MD, USA).

Analysis of Vorinostat in Mice $Npc1^{+/nmf164}$ mice (age 6-7 weeks) were injected with either vorinostat (50 mg/kg) in PEG or TCF through i.p route. Mice were sacrificed 1 hpi by asphyxiation using $CO_2$. Total blood was collected through cardiac puncture in the presence of 100 μl heparin and transferred to $K_2EDTA$ microtainer tubes (VWR International, Chicago, Ill., USA). Blood was immediately spun at 1500 g at 4° C. for 15 min. Plasma was transferred to a separate tube, immediately flash-frozen in liquid nitrogen and stored at −80° C. until analyzed.

For the analysis of vorinostat, to a volume of 50 μl of plasma 2 ng of deuterated internal standard ($d_5$-Vorinostat, Toronto Research Chemicals, Ontario, Canada) was added prior to liquid extraction. To each, 1 ml of cold acetonitrile was added to precipitate the protein before collecting the supernatant and drying using a vacuum concentrator system. Prior to HPLC/MS/MS analysis, each sample was reconstituted in 100 μL of 50% water/50% acetonitrile. An Agilent 1200 Rapid Resolution liquid chromatography (HPLC) system coupled to an Agilent 6460 series QQQ mass spectrometer (MS/MS) was used to analyze Vorinostat in each sample. An Agilent Zorbax XBD-C18 2.1 mm×50 mm, 3.5 μm column (Agilent Technologies, Santa Clara, Calif.) was used for HPLC separation. The buffers were (A) water+0.1% formic acid and (B) acetonitrile+0.1% formic acid. The linear LC gradient was as follows: time 0 minutes, 5% B; time 1 minute, 5% B; time 10 minutes, 95% B; time 11 minutes, 95% B; time 12 minutes, 5% B; time 15 minutes, 5% B. Retention time for Vorinostat/$d_5$-Vorinostat was 6.7 minutes. Multiple reaction monitoring was used for MS/MS analysis. The data were acquired in positive electrospray ionization (ESI) mode by monitoring the following transitions for Vorinostat: 265→232 with collision energy of 5 V, 265→172 with collision energy of 5 V, and 265→55 with collision energy of 40 V. For $d_5$-Vorinostat, data were acquired by monitoring the following transitions: 270→237 with collision energy of 5 V, 270→172 with collision energy of 5 V, and 270→55 with collision energy of 40V. The jet stream ESI interface had a gas temperature of 325° C., gas flow rate of 8 L/minute, nebulizer pressure of 45 psi, sheath gas temperature of 275° C., sheath gas flow rate of 7 L/minute, capillary voltage of 4000 V, and nozzle voltage of 1000 V. All data were acquired and analyzed using Agilent MassHunter software (version B.06). In the final drug calculation in mice plasma, contribution of heparin to total volume was subtracted before plotting the numbers.

Neurobehavioral Assessment of Mice

A modified version of previously described method (Carroll et al., 2010) was used for assessing the neurobehavioral functions in mice. Six different parameters (FIG. 3A) associated with neurobehavioral functions of mice were assessed. Each mouse was assessed individually in an observation box (length, 31.8 cm, width, 19.8 cm and height, 10.5 cm) with a grid floor. A mouse was assessed for tremor (0 and 2), body position (0, 1 and 2), gait (0, 1 and 2), grooming (0, 1 and 2), limb tone (0, 1 and 2), and weight loss (0, 1, 2 and 3). More specific descriptions of the assessments along with the equivalent human symptoms are provided in the FIG. 3A. For each symptom except weight, a mouse received a score 0 if no symptom was observed and score 2 when the most severe impairment in the function was seen. A mouse was given score 0 for weight loss below 5%, 1 for 5-10%, 2 for >10 and up to 20%, and 3 for >20 up to 30%. A cumulative score of 0-3 correlate with no neurobehavioral impairment and a score of 13 is the most impaired neurobehavioral function. Operator-independence scoring was also tested by two independent blinded operators on 6 NPC ($Npc1^{nmf164}$) and 4 healthy control ($Npc1^{+/nmf164}$) mice.

Statistical Tests

Log-rank test was undertaken to determine the statistical significance. Unless mentioned, results shown are mean±SEM. Student's t test was carried out to determine the statistical significance of the data using two tail analyses. $P<0.05$ considered significant.

Results

Cell-based studies have previously shown that HDACi's reduce cellular cholesterol in NPC cells in tissue culture with concomitant increase in expression of NPC1, but the effects in whole animals have not been investigated. We utilized $Npc1^{nmf164}$ a BALB/c strain (Alam et al., 2014) derived from the recently described $Npc1^{nmf164}$ in C57BL/6J (Maue et al., 2012). The mutation is a single nucleotide change (A to G at cDNA by 3163) resulting in an aspartate to glycine change at position 1005 (D1005G), which destabilizes the protein resulting in partial loss of activity and levels of NPC1. Disease progression in this model (monitored over ~120 days) closely mimics human disease, where neurodegeneration is the principal cause of death.

As shown in FIG. 1A, skin fibroblasts from mutant $Npc1^{nmf164}$ animals express lower levels of NPC1 protein compared to heterozygote or wild type counterparts. Mutant fibroblasts therefore accumulate high levels of cholesterol, which are reduced in presence of vorinostat (FIG. 1B) confirming cellular responsiveness to HDACi therapy. To treat animals we selected a conservative dose of 50 mg/Kg vorinostat, significantly lower (by 100-200%) than levels used to treat murine models of cancers. Scaling translated 50 mg/Kg in mice to 150 mg/m² in children, which is well below reported total weekly human intravenous pediatric doses of 396 mg/m². Since we expected to monitor survival over several months, injection frequency was limited to once weekly. This also enabled a desired (weekly) rest period, since continuous HDAC inhibition may be detrimental to neurological (especially cerebellar) function. Vorinostat solubilized in polyethylene glycol 400 (PEG) was first administered at day 21 after weaning and maintained once weekly through the animal's life span. At 50 /mg/Kg in mice, there was no significant beneficial effect on animal survival (FIG. 1C). Increasing the dose by two-fold to 100 mg/Kg in mice or (equivalent to 300 mg/m² human dose) also conveyed no survival benefit (FIG. 1C). These data suggested that at despite vorinostat's activity with cultured cells, weekly doses approaching those in pediatric patients were insufficient to reduce neurological disease in mice even after four months of treatment that began from immediately after weaning and was maintained throughout the animal life span.

Vorinostat is poorly soluble in aqueous solution and therefore is classified as a Biopharmaceutical Classification System (BCS) class 4 drug (http://www.accessdata.fda). We reasoned that its rapid clearance from plasma could limit exposure and therefore effective penetration of the blood brain barrier. We therefore developed a formulation where a low level of vorinostat (50 mg/Kg) in PEG was complexed with HPBCD (2000 mg/Kg) (in a final molar ratio of 0.13), to create a triple combination formulation (TCF; schematically represented in FIG. 1D). We selected HPBCD because it has a hydrophobic interior core and hydrophilic exterior surface and complexes with hydrophobic compounds to enhance their solubility and bioavailability. In addition, when delivered systemically, although it does not cross the blood brain barrier, HPBCD improves liver disease and at high concentrations of 4000 mg/Kg also partially benefits neurological disease largely by promoting anti-inflammatory effects. It is therefore expected to benefit liver (and other systemic) disease through indirect mechanisms and complement vorinostat's direct effects (of npc1 expression). PEG was retained to facilitate release of vorinostat from HPBCD and improve bioavailability. PEG may also contribute to reducing BBB inflammation by improving healing of ruptured endothelial membranes.

Figure 7:
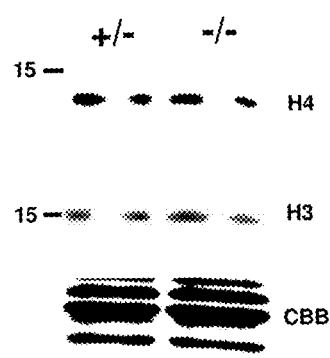
FIG. 7 presents data showing the acetylation levels of histone H3 and H4 in the brain of NPC mice were similar to healthy mice.

The TCF containing vorinostat, HPBCD, and PEG was designed to circumvent CNS delivery but yet treat both neurological and systemic disease. As shown in FIG. 1E-F within an hour of administration through intraperitoneal (i.p.) route, neither vehicle control (PEG+DMSO) nor HPBCD stimulated significant acetylation of either histone 3 or 4 (H3 or H4) in the brain. Vorinostat (50 mg/Kg) in PEG conferred low levels of acetylation, but upon administration of TCF acetylation was stimulated to 2-3 fold ($p<0.05$) for histone H3 and 5-9 fold ($p<0.05$) for H4 (FIG. 1E-F). The basal levels of acetylated histone H3 and H4 in the brain of NPC mice were similar to healthy heterozygous mutant mice (FIG. 7). These data establish that the TCF stimulated a functional productive level of vorinostat activity as measured by increased histone acetylation, in the brain, suggesting improved potential to treat neurological disease.

Figure 8:
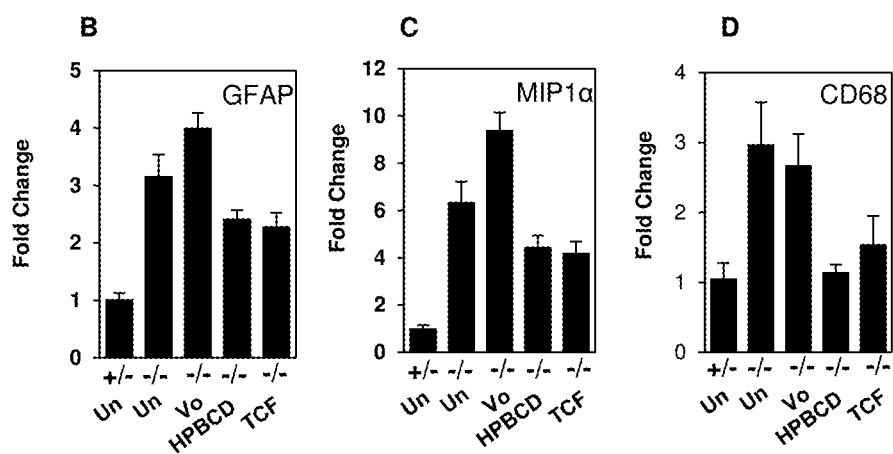
FIG. 8 presents a qPCR analysis of various inflammatory markers as indicated in the brain of drug treated Npc1$^{nmf164}$ mice at 100 days.

To compare the effects of long term treatment, mice were given a once weekly dose of TCF or 4000 mg/Kg HPBCD (also referred to as 2×HPBCD since it represents twice the levels incorporated in TCF), 50 mg/Kg vorinostat in PEG or a mock injection (PEG+DMSO). Comparative analyses of animal tissues were undertaken at day 100, since prior studies suggest this to be a period of symptomatic disease (untreated Npc1$^{nmf164}$ mice succumb to death by ~125 days). As shown in FIG. 2A, in the brain, the TCF stimulated increased expression of calbindin, a marker of Purkinjie cell bodies and neurites extending to the molecular layer in the cerebellum. Vorinostat alone or 2×HPBCD showed no change or depressed levels of calbindin transcripts. Consistently, the TCF restored 25-30% of Purkinje cells ($p<0.001$) while vorinostat alone had no effect (FIG. 2B). 2×HPBCD, conferred a minor protection of Purkinje cell, the mechanism for which is unknown but which is not due to HPBCD crossing the BBB. Analyses of three inflammatory markers, GFAP, MIP1α and CD68 suggested that 2×HPBCD reduced their levels comparably to TCF and better than Vo in the brain (FIG. 8). This is again consistent with prior studies that HPBCD is partially effective in reducing neuroinflammation. Moreover our data suggest that vorinostat and HPBCD in TCF may act synergistically in reducing neuroinflammation, since the combination is far more efficacious than 2×HPBCD (expected to be additive relative to HPBCD alone). Therefore in summary, by combining data on acetylation activity in the brain and histopathological analyses, we conclude that TCF's capacity of neurological protection was associated with increased vorinostat activity in the brain and combined effects of vorinostat and HPBCD to comprehensively reduce inflammation (FIG. 8).

We next assessed whether improvement in cerebral pathology could be correlated with improved survival, a critical criterion for a fatal neurodegenerative condition. As shown in FIG. 2C, the median life span of TCF-treated mice was ~200% that of animals treated with vorinostat in PEG (254 vs 134 d, $p<0.001$). In contrast 2×HPBCD increased survival by a third (180 vs 134 d, $p<0.001$), while vorinostat alone or vehicle treated animals showed no significant survival benefit. TCF was equally effective against both sexes of mice with comparable median survival for males (249 d) and females (258 d; FIG. 2D, E). TCF-treated animals can survive up to nine to ten months, which is notable in context that mice in this time frame are well into advanced adulthood. The improved survival of TCF-treated animals correlated with the action of the triple combination in stimulating vorinostat activity in the brain and preventing neurodegeneration.

Clinically NPC disease is defined by major and minor symptomatic domains, whose severity has been scored to monitor the natural history of the disease using at least three different scales. Plasma biomarkers are emerging, but quantitative assessment of symptoms continues to be an important index of disease progression and their aggregation in a cumulative score provides a valuable overall outcomes measure. We extended a previously described murine neurobehavioral symptomatic score to create a disease severity scale for murine NPC with the main correlates of human disease (FIG. 3A). As shown, each of the six symptomatic parameters in the mouse was assigned to a major patient disease domain (ambulation, cognition, motor control and dysphagia), scored for severity in an indicated range. The sum of the individual scores provided the cumulate disease score, with a maximal possible disease score of 13.

Figure 9:
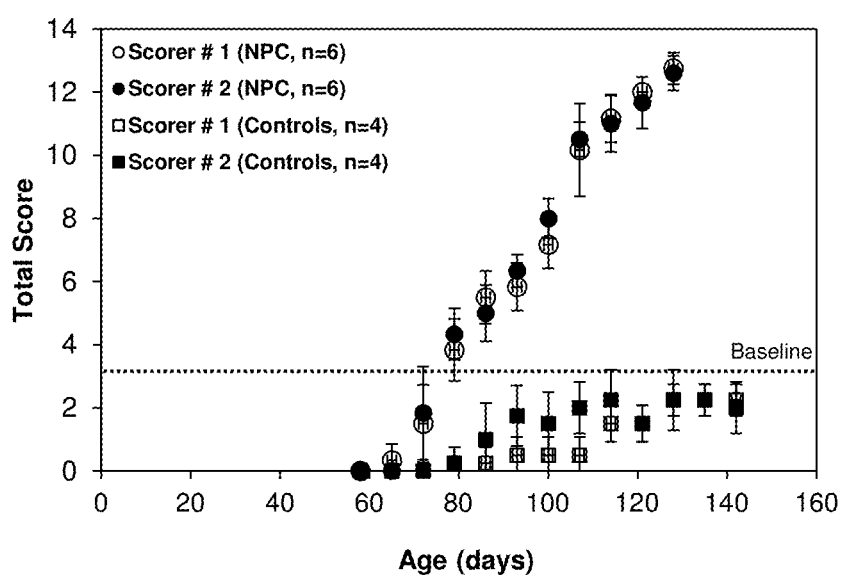
FIG. 9 presents neurobehavioral scoring of NPC and healthy mice and operator independence.

Validation of scoring by independent blinded operators in both diseased and healthy animals is shown in FIG. 9. A cumulative score of 3 or higher was found to reliably flag onset of symptomatic disease. A threshold of 3 was encountered because older healthy animals often displayed poor grooming (particularly males) and slight impairment in limb tone (from days 100-140 days). It was nonetheless acceptable and using these criteria, an early cumulative disease score of 4-5 reliably detected the onset of symptomatic disease in untreated animals at 77-84 days (FIG. 3A). TCF treatment appeared to delay disease onset by ~4 weeks reaching scores 4-5 at 105-112 days. At this time, vehicle or vorinostat alone treatment resulted in cumulative scores of 9-11, while 2×HPBCD yielded intermediate, cumulative scores of 6-8 (FIG. 3A). Analysis of individual symptomatic domains revealed that worsening in gait, grooming, limb tone and weight were all delayed in animals treated with the TCF (FIG. 3B). Worsening in gait, grooming and weight were also delayed by 2×HPBCD, but less so than by the TCF. Vorinostat provided no consistent, significant advantage in any symptomatic read out in context of lifespan. These data suggest that TCF administration affords significant benefit to ambulation, cognition, motor control and dysphagia, major symptomatic domains in neurological disease. In particular the animals maintained their weight even at terminal stages of disease, suggesting they retained the ability to drink water by delay of dysphagia (in murine NPC terminal disease is marked by dehydration seen as weight loss; FIG. 3B).

We also examined the consequences of treatment to the liver (FIG. 4), as an example of an organ outside of the BBB (and in the mouse, the liver disease is prominent in NPC). After 100 days of treatment, histological analyses suggested that the TCF supports reduced macrophage recruitment to the same degree as HPBCD (FIG. 4A). Vorinostat also had effect but less so than TCF or HPBCD. TCF reduced the inflammatory markers CD68, ITGAX, MIP1α and CTSD, comparable to HPBCD although the presence of vorinostat in TCF appears to further reduce CD68 transcripts (FIG. 4B-E). Vorinostat alone also had significant anti-inflammatory activity. These data suggested that vorinostat may reduce systemic disease without providing neurological benefit. Moreover, in conjunction with the findings in FIGS. 2 and 3, they strongly support that vorinostat needs to be administered in the TCF form to also treat neurological disease and improve animal survival.

To investigate a mechanistic basis for the observed effects of TCF, we compared the plasma concentrations realized for vorinostat and the expression of Npc1. As shown in FIG. 5A, in mice treated with TCF, within 1 hr, the concentrations is plasma were 2-3 fold ($p<0.05$) higher than animals injected with vorinostat alone. Since disease progression extends over 120 days (in absence of treatment) we further examined evidence for direct mechanism of action at 100 days (which our survival and symptomatic data confirm corresponds to late stage disease). We found that animals treated with TCF showed higher levels of stably expressed Npc1 transcript in the liver at 100 days (FIG. 5B; as expected HPBCD alone had no effect on target Npc1 expression). In the brain, the TCF treatment significantly increased levels of Npc1 transcript (FIG. 5C). But there was little or no effect on brain Npc1 transcript levels after administration of either HPBCD or vorinostat in PEG. Therefore, although vorinostat alone may stimulate low levels of histone acetylation in the brain (shown earlier in FIG. 1E-F), this is insufficient for stimulating transcriptional expression of Npc1 needed for longer term benefit. Rather the benefit of sustained Npc1 transcript expression throughout treatment in both liver and brain requires stimulation of acetylation activity induced by vorinostat in TCF.

Finally, since the deleterious effect of HDAC knock down on Purikinje cells and cerebellar function has been reported in the literature, we examined NPC1 protein expression in the cerebellum of TCF treated mice. As shown in FIG. 5D, immunostaining of brain sections (with antibodies to NPC1) showed fivefold increase of rescue of NPC1 in Purkinje cells in the cerebellum of TCF-treated mice compared to untreated animals at 100 days This reflects as much as 25% of NPC1 staining in the Purkinje cells compared to control, heterozygous healthy mice. Notably at this 100 day time point, TCF treated mice remain largely asymptomatic (FIG. 3) suggesting even partial rescue of cerebellar Purkinje cells can be highly beneficial.

Although additional characterization of this treatment model is possible and ongoing, our data provide robust evidence for proof of concept for a model (FIG. 6) in which systemic delivery of the formulation increases plasma concentration of the HDACi, to stimulate HDACi activity with direct mechanism of action in the brain and rest of the body. Although our data are collected for NPC, we propose this model is generalizable to other diseases, where the TCF, by increasing the molecular target gene and combining other indirect benefits (such as through increase in heat shock proteins or other chaperones) including those afforded by circulating HPBCD, synergizes distinct beneficial mechanisms to treat cerebral and systemic disease.

FIG. 1. Comparative analyses of vorinostat alone (Vo; in PEG) and in the triple combination formulation in the Npc1$^{164}$ mice.

A. NPC1 protein detected in western blots of cultured mouse skin fibroblasts isolated from wild type, Npc1$^{+/nmf164}$ (heterozygous mutant) and Npc1$^{nmf164}$ (NPC) mice, Loading control, tubulin.

B. In vitro grown skin fibroblasts from Npc1$^{nmf164}$ mice treated with 5 μM Vo for 48 hrs, and labeled with filipin. Cholesterol accumulation was seen in NPC cells that were untreated or exposed to solvent alone. Vorinostat decreased cholesterol levels in NPC cells to those seen in fibroblasts from control (Npc1$^{+/nmf164}$) mice. Three independent experiments were done in duplicate wells.

C. Npc1$^{nmf164}$ mice were administered with vorinostat at 50 mg/kg (Vo, 1×) or 100 mg/kg (Vo, 2×), vehicle i.p. once weekly or left uninjected. Number of mice as indicated.

D. Schematic of the Triple Combination Formulation (TCF).

E. Western blots detect acetylation of histones 3 and 4 (H3 and H4) in the brain of Npc1$^{nmf164}$ mice within 60 min after drug administration. Coomassie stained gel (CBB; blue) confirms equal loading of all samples.

F. Quantitation of data in E. Vo, Vorinostat (50 mg/Kg) in 45% PEG; HPBCD, 2-hydroxypropyl beta cylcodextrin (2000 mg/Kg); TCF, Triple Combination Formulation (Vorinostat, 50 mg/Kg+HPBCD, 2000 mg/Kg+45% PEG); Vehicle, DMSO (5%)+PEG400 (45%). Un, untreated Npc1$^{nmf164}$ mice.

Figure 2:
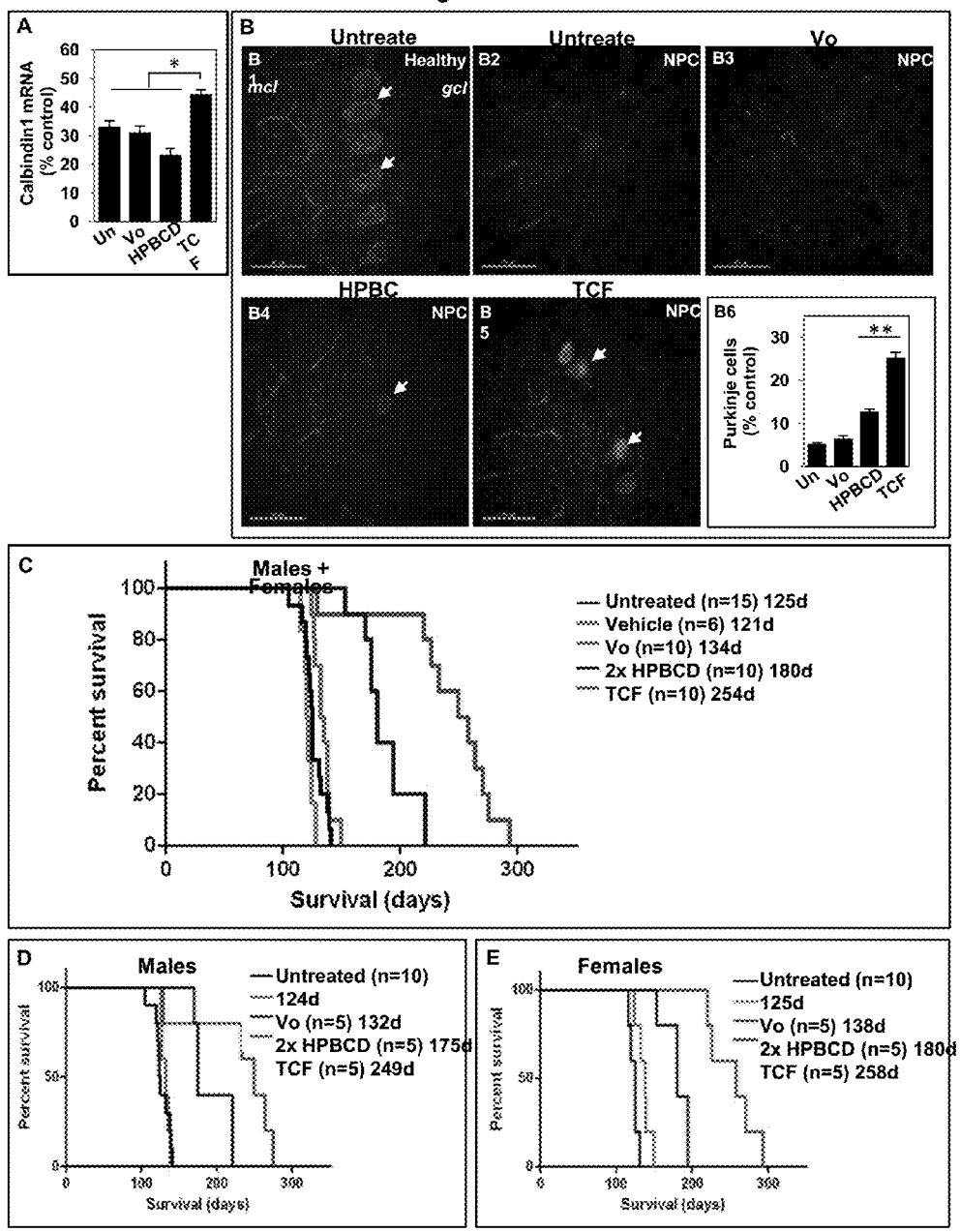
FIG. 2 shows analyses of comparative composition and an exemplary embodiment in neurodegeneration and animal survival.

FIG. 2. Comparative effects of TCF and its component reagents on neurodegeneration and animal survival.

A. Relative expression of Calbindin1 transcripts in the brain of drug treated Npc1$^{nmf164}$ mice at 100 days. The level of Calbindin1 transcript in untreated healthy control mice (Npc1$^{+/nmf164}$) was set at 100% and amount in other animals are shown relative to that. Each group consisted of 4-5 mice.

B1-B5. Fluorescence micrographs showing the presence of Purkinje cells and calbindin positive neuritis in the cerebellar section of Npc1$^{nmf164}$ mice treated with different drugs at 100 days. Brain sections were stained using anti-mouse calbindin antibodies. Purkinje cells (stained in green) indicated by white arrows are evident in healthy control (B1). Loss of Purkinje cells in the cerebellum of untreated and Vo injected NPC mice (B2&B3). Few lightly stained Purkinje cells (indicated by arrow) and slight calbindin positive neurite staining in the molecular layer of the cerebellum were seen in the mice injected with HPBCD (B4). Several Purkinje cells (indicated by arrows) and enhanced calbindin positive neuritis in the molecular layer were seen in TCF treated mice (B5). Micrographs shown are representative images of IX lobule of the cerebellum from 4 mice in each group. Calbindin, green; DAPI, blue; original magnifications×40. Scale bar, 40 μm. (B6) Semi-quantitative analysis of Purkinje cells in the cerebellum of drug treated Npc1$^{nmf164}$ mice at 100 days. Numbers of Purkinje cells in the calbindin labeled cerebellar sections (4 sections per mouse, 4 mice in each group) were counted. The data represent the percentage of Purkinje cells relative to untreated healthy control mice (Npc1$^{+/nmf164}$) which was set at 100%.

C-E. Kaplan-Meier survival curves of untreated and drug treated (A) Npc1$^{nmf164}$ mice, males and females combined (B) male Npc1$^{nmf164}$ and (C) female Npc1$^{nmf164}$ mice. Mice were given weekly injections through i.p route (see Materials and Methods). Median survival (days) is indicated for each group. Log-rank test was performed to determine the statistical significance. *p<0.001 vs 2×HPBCD; n, number of mice; d, days.

Vo, Vorinostat (50 mg/Kg) in 45% PEG; HPBCD, 2-hydroxypropyl beta cylcodextrin (2000 mg/Kg); 2×HPBCD, 2-hydroxypropyl beta cylcodextrin (4000 mg/Kg); TCF, Triple Combination Formulation (Vorinostat, 50 mg/Kg+ HPBCD, 2000 mg/Kg+45% PEG); Vehicle, DMSO (5%)+ PEG400 (45%). Un, untreated Npc1$^{nmf164}$ mice.

Figure 3:
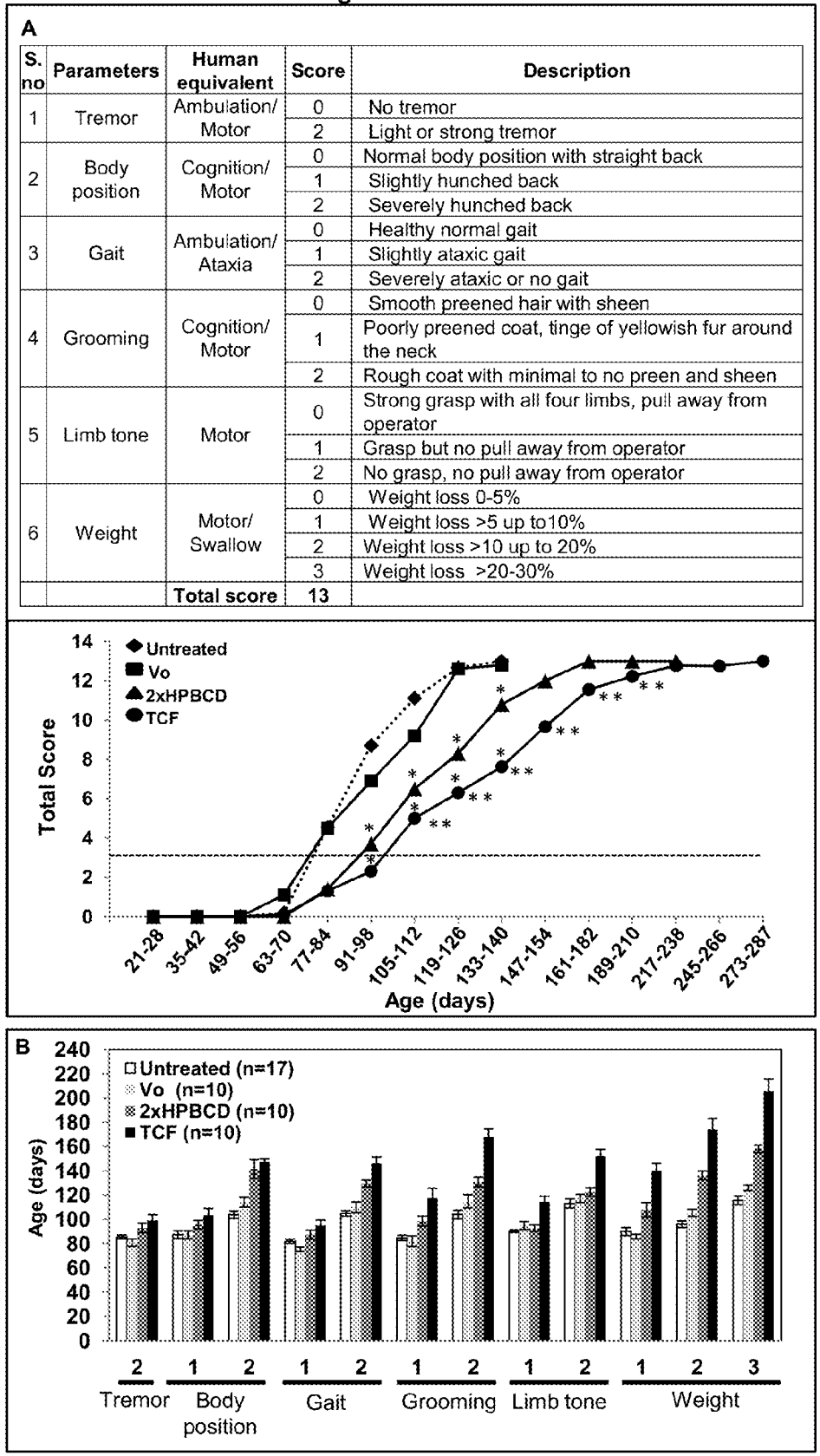
FIG. 3 shows a murine neurobehavorial disease score for NPC and analyses of comparative composition and an exemplary embodiment Npc1$^{nmf164}$ mice.
Figure 4:
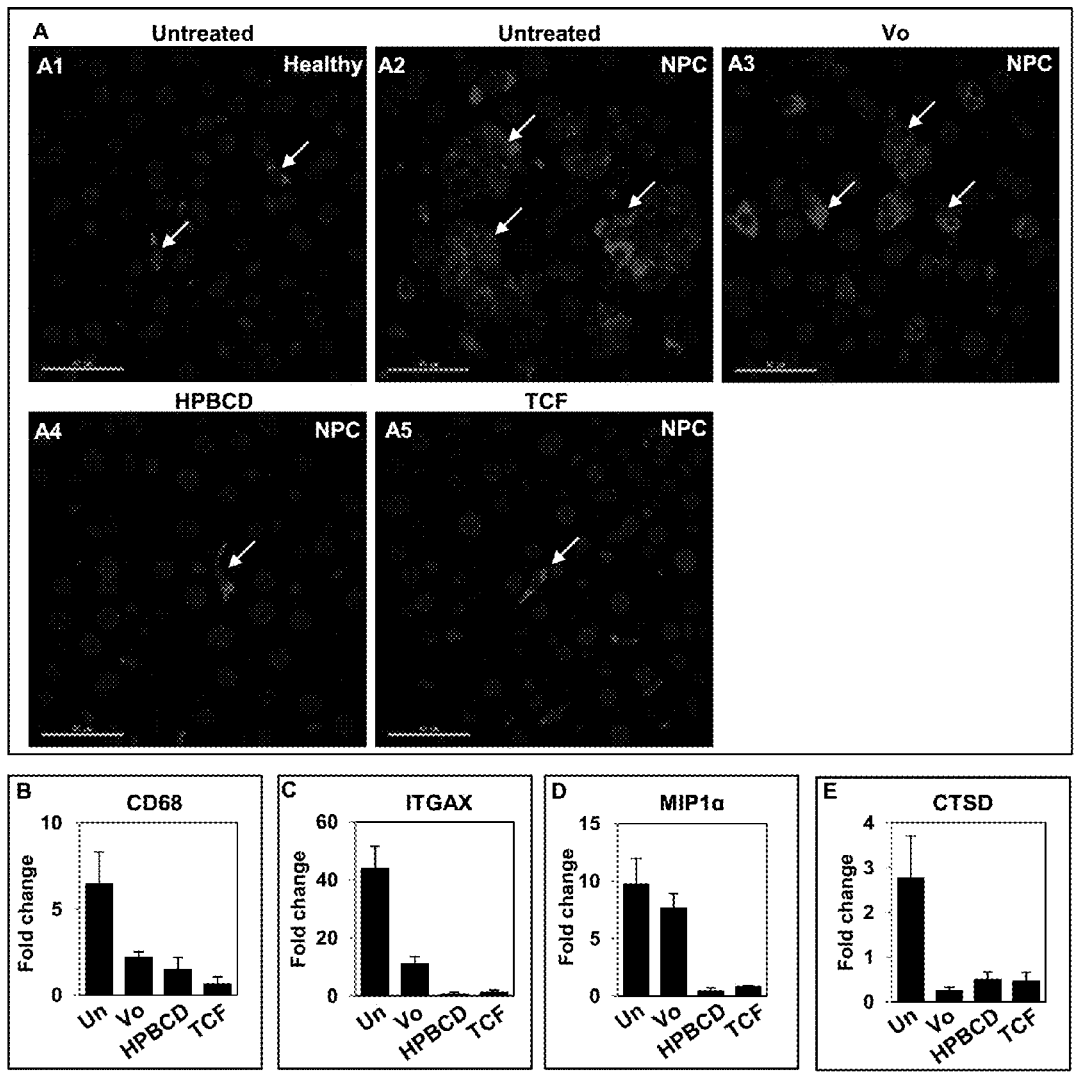
FIG. 4 shows analyses of comparative composition and an exemplary embodiment in liver inflammation in Npc1$^{nmf164}$ mice.

FIG. 3. Murine neurobehavorial disease score for NPC and effects of the TCF in Npc1$^{nmf164}$ mice.

A. List of parameters used to test the neurobehavioral function of Npc1$^{nmf164}$ mice (upper panel). Line curves (lower panel) show the progression of cumulative neurobehavioral score of mice. Mice were treated with different drugs and their neurobehavioral functions were assessed every other week on a cumulative score of 0-13 starting at 3 weeks of age.

B. Bar diagrams display the age of onset of individual symptoms in untreated and drug treated Npc1$^{nmf164}$ mice.

Vo, Vorinostat (50 mg/Kg) in 45% PEG; 2×HPBCD, 2-hydroxypropyl beta cylcodextrin (4000 mg/Kg); Vo, TCF, Triple Combination Formulation (HPBCD, 2000 mg/Kg+ Vorinostat, 50 mg/Kg+45% PEG), Vehicle, DMSO (5%)+ PEG400 (45%). *p<0.05 (treated vs untreated), **p<0.05 (TCF vs 2×HPBCD).

FIG. 4. Comparative analyses of Vo and TCF on liver inflammation in Npc1$^{nmf164}$ mice.

A. Fluorescence micrographs showing the labeling of macrophages in the liver of Npc1$^{nmf164}$ mice. Liver sections (4-5 μm) from 100 days old mice were stained with anti-CTSS antibodies to stain macrophages (in red) which are indicated by white arrows. Macrophages were seen in abundance often in clusters in untreated NPC mice. Treatment with Vo reduced the clustering of macrophages. Foamy macrophages were barely seen in HPBCD and TCF treated NPC mice. CTSS, green; DAPI, blue. Original magnifications×40.

B-E. qPCR analysis of various inflammatory markers as indicated in the liver of drug treated Npc1$^{nmf164}$ mice at 100 days. Fold change shown is relative to average levels of transcripts detected in untreated healthy control (Npc1$^{+/nmf164}$) mice. Each group consisted of 4-5 mice. The data represent mean±SEM.

Vo, Vorinostat (50 mg/Kg) in 45% PEG; HPBCD, 2-hydroxypropyl beta cylcodextrin (2000 mg/Kg); TCF, Triple Combination Formulation (HPBCD, 2000 mg/Kg+Vorinostat, 50 mg/Kg+45% PEG), Vehicle, DMSO (5%)+PEG400 (45%). Un, untreated Npc1$^{nmf164}$ mice.

Figure 5:
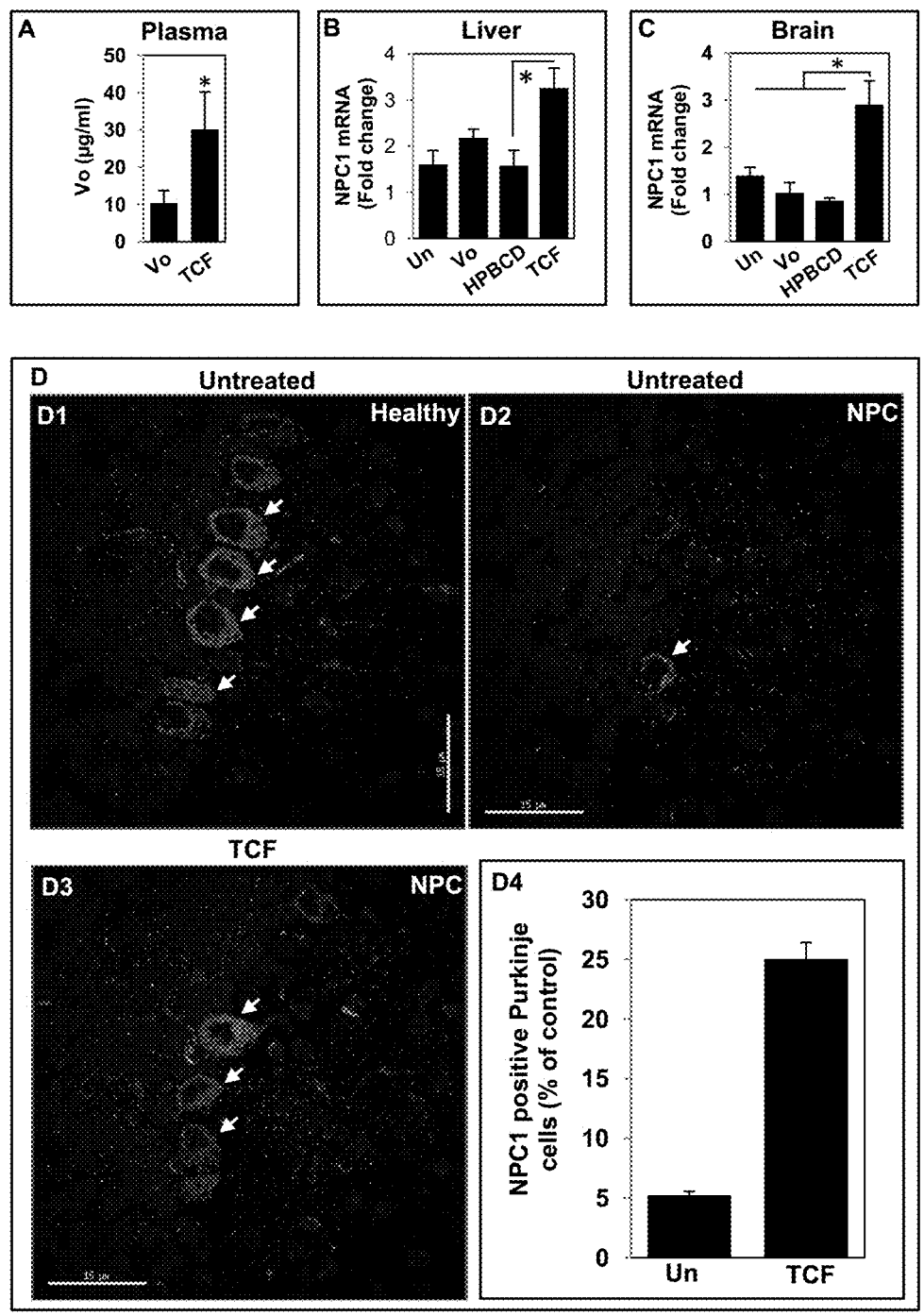
FIG. 5 shows analyses of comparative composition and an exemplary embodiment in plasma, liver, and brain in Npc1$^{nmf164}$ mice.

FIG. 5. Mechanism of TCF action.

A. Plasma Vo concentration in mice. Npc1 heterozygous mutant mice (Npc1$^{+/nmf164}$) were injected with Vo or TCF through i.p route. Blood was sampled through cardiac puncture at 1 hpi and concentration of Vo in the plasma was determined by mass spectrometry. The data represent mean±SEM from two independent experiments (5 mice/ group in each experiment). *p<0.05, TCF vs Vo.

B-C. Quantitative PCR showing the amount of NPC1 transcripts in (B) liver and (C) brain of drug treated Npc1$^{+/nmf164}$ mice at 100 days. The fold change is relative to untreated healthy control (Npc1$^{+/nmf164}$) mice. Each group consisted of 4-5 mice. *p<0.05, TCF vs HPBCD.

D. Immunofluorescence micrograph of cerebellar sections showing labeling of NPC1 protein in the Purkinje cells. Brain sections from 100 days old mice were stained using anti-NPC1 antibodies. Prominent NPC1 staining was seen in the Purkinje cells (stained in green) indicated by white arrows are evident in healthy control (D1). Slight staining of NPC1 was seen in the Vo treated mice (D2). Numerous Purkinje cells expressing NPC1 protein were seen in the Purkinje cells of TCF treated mice. Micrographs shown are representative images of IX lobule of the cerebellum from 2 mice in untreated and 4 mice in TCF treated mice. 4 sections from each mouse were analyzed. NPC1, green; DAPI, blue; original magnifications×40. D6. Semi-quantitative analyses of NPC1 positive Purkinje cells. Number of NPC1 positive Purkinje cells in cerebellar sections (4 sections per mouse, 2 mice in untreated and 4 mice in TCF treated group) was counted. The data represent the percentage of NPC1 positive Purkinje cells relative to untreated healthy control mice (Npc1$^{+/nmf164}$) which was set at 100%.

Vo, Vorinostat (50 mg/Kg) in 45% PEG; HPBCD, 2-hydroxypropyl beta cylcodextrin (2000 mg/Kg); TCF, Triple Combination Formulation (HPBCD, 2000 mg/Kg+Vorinostat, 50 mg/Kg+45% PEG); Un, untreated Npc1$^{nmf164}$ mice.

Figure 6:
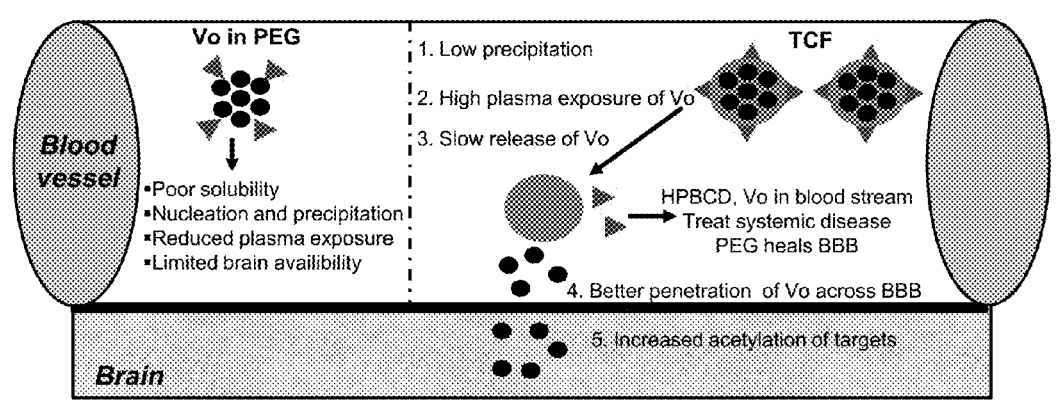

FIG. 6. Proposed model for TCF in treating cerebral and systemic disease. Vorinostat (Vo) solubilized in PEG when injected into the animals has poor solubility and reduced plasma exposure which significantly limits its penetration across the blood brain barrier (BBB). On the other hand, delivery of Vo in TCF leads to better solubility, low precipitation and high plasma exposure. TCF may also allow slow release of Vo from the complex. In addition, TCF also significantly improves its penetration across the blood BBB. Vo in brain at upon the target proteins (histones and others) and induces gene transcription. Npc1 gene is one of them. Vo also directly or indirectly (through involvement of chaperones) stabilize and over express the mutant NPC1 protein. HPBCD and Vo in blood stream treat systemic disease whereas PEG helps in reducing endothelial inflammation by promoting plasma membrane repair.

FIG. 7. The acetylation level of histone H3 and H4 in the brain of NPC mice were similar to healthy mice. Brain was harvested from 6-7 weeks old Npc1$^{nmf164}$ (n=2) and Npc1$^{+/nmf164}$ (healthy, n=2) mice and total histones were extracted and probed with antibodies to acetylated H3 and H4, as shown. Coomassie (CBB) stained gel (blue) run in parallel shown below confirms equal levels of histones were loaded in each lane (as loading controls).

FIG. 8. qPCR analysis of various inflammatory markers as indicated in the brain of drug treated Npc1$^{nmf164}$ mice at 100 days. Fold change shown is relative to average levels of transcripts detected in untreated healthy control (Npc1$^{-/nmf164}$) mice. Gapdh was used as endogenous control. Each group consisted of 4-5 mice. The data represent mean±SEM. Vo, Vorinostat (50 mg/Kg) in 45% PEG; HPBCD, 2-hydroxypropyl beta cylcodextrin (2000 mg/Kg); TCF, Triple Combination Formulation (HPBCD, 2000 mg/Kg+Vorinostat, 50 mg/Kg+45% PEG). Un, untreated Npc1$^{nmf164}$ mice.

FIG. 8. Neurobehavioral scoring of NPC and healthy mice and operator independence. Two blinded investigator weekly scored 10 mice (6 Npc1$^{nmf164}$ and 4 Npc1$^{+/nmf164}$, all males) from 8 weeks onwards until death. Investigators scored the mice on two different days (a day apart). Six different parameters namely, tremor, body position, gait, grooming, limb tone, weight were assessed on a cumulative score of 0-13. All parameters were scored on a scale of 0-2 except weight which was assessed on scale of 0-3. Score above 3 (baseline, shown by dotted line) suggested diseased state.

Histone deacetylase inhibitors are approved as therapies for rare cancers. They are also of interest in neurodegenerative disorders with a paucity of therapies. However, brain function, and particularly cerebellar Purkinje cells require HDAC activity. The inventors examined a mouse model of a difficult-to-treat cerebellar disorder, Niemann Pick Type C, administered with a composition (TCF) containing the pan HDACi vorinostat, 2-hydroxylpropyl-beta-cyclodextrin (HPBCD), and polyethylene glycol (PEG). Vorinostat, although active against cultured primary mouse cells from Npc1$^{nmf164}$ mice, when injected into animals showed no survival benefit. In contrast, the TCF administered once weekly significantly improved brain protein acetylation and preservation of neurites and Purkinje cells, broadly delayed symptoms of neurodegeneration and extended mouse life span from four to almost nine months. The TCF increased the plasma concentration of vorinostat, as well as npc1 transcript levels in liver (an index of systemic expression) and brain. Importantly, and surprisingly, increased levels of NPC1 protein were observed in preserved cerebellar Purkinje cells. The present study suggests that the TCF improves HDACi access across the blood brain barrier and proves that an HDACi formulation and regimen can significantly benefit overall cerebral disease as well as cerebellar Purkinje cells and neurites. Therefore, the TCF presents unique promise as superior therapy integrated to treat both cerebral and systemic disease in Niemann Pick Type C with potential for translation to other challenging disorders.

Given the description herein, combined with the knowledge of one of ordinary skill in the art to which the invention pertains, any embodiment described herein can be readily accomplished, carried out, and/or further implemented with respect to any use, method, compound, composition, kit, obvious variant thereof, or any combination thereof.

Further, although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method for treating Niemann-Pick Type C disease in a subject, comprising administering to the subject a pharmaceutical composition, comprising:
   vorinostat;
   2-hydroxypropyl-β-cyclodextrin, prodrug thereof, salt thereof, or a combination thereof;
   polyethylene glycol 400;
   DMSO;
   and water;
   wherein the polyethylene glycol 400 is present in an amount of 30-55% by weight, based on the weight of the composition; and
   wherein the composition comprises a molar ratio of vorinostat:2-hydroxypropyl-β-cyclodextrin:polyethylene glycol 400 of 1:1-10:10-70.

2. The method of claim 1, wherein the composition is administered in an amount such that vorinostat is administered in an amount of 0.1-500 mg/kg, based on the weight of the subject.

3. The method of claim 1, wherein the composition is administered in an amount such that 2-hydroxypropyl-β-cyclodextrin is administered in an amount of 1000-40,000 mg/kg, based on the weight of the subject.

4. A pharmaceutical composition, comprising:
   vorinostat;
   2-hydroxypropyl-β-cyclodextrin, prodrug thereof, salt thereof, or a combination thereof;
   polyethylene glycol 400;
   DMSO;
   and water;
   wherein the polyethylene glycol 400 is present in an amount of 30-55% by weight, based on the weight of the composition; and
   wherein the composition comprises a molar ratio of vorinostat: 2-hydroxypropyl-β-cyclodextrin:polyethylene glycol 400 of 1:1-10:10-70.

5. The composition of claim 4, wherein the molar ratio of vorinostat: 2-hydroxypropyl-β-cyclodextrin:polyethylene glycol 400 is 1:3-10:15-70.

6. The composition of claim 4, wherein the molar ratio of vorinostat: 2-hydroxypropyl-β-cyclodextrin:polyethylene glycol 400 is 1:3-8:15-70.

7. The composition of claim 4, wherein the molar ratio of vorinostat: 2-hydroxypropyl-β-cyclodextrin:polyethylene glycol 400 is 1:3-8:15-35.

8. The composition of claim 4, wherein the polyethylene glycol 400 is present in an amount of 35-55% by weight, based on the weight of the composition.

9. The composition of claim 4, wherein the polyethylene glycol 400 is present in an amount of 35-50% by weight, based on the weight of the composition.

10. The composition of claim 4, wherein the polyethylene glycol 400 is present in an amount of 40-50% by weight, based on the weight of the composition.

11. The composition of claim 4, wherein the 2-hydroxypropyl-β-cyclodextrin has an average molecular weight of 1396 Da.

12. The composition of claim 4, wherein the 2-hydroxypropyl-β-cyclodextrin has an average degree of substitution of 0.67 hydroxypropyl groups per glucopyranose unit.

13. The composition of claim 4, which comprises 2-hydroxypropyl-β-cyclodextrin.

14. The composition of claim 4, wherein the DMSO is present in an amount of 5% by weight, based on the weight of the composition.

15. The method of claim 1, wherein the molar ratio of vorinostat: 2-hydroxypropyl-β-cyclodextrin:polyethylene glycol 400 is 1:3-10:15-70.

16. The method of claim 1, wherein the molar ratio of vorinostat: 2-hydroxypropyl-β-cyclodextrin:polyethylene glycol 400 is 1:3-8:15-70.

17. The method of claim 1, wherein the molar ratio of vorinostat: 2-hydroxypropyl-β-cyclodextrin:polyethylene glycol 400 is 1:3-8:15-35.

18. The method of claim 1, wherein the polyethylene glycol 400 is present in an amount of 35-55% by weight, based on the weight of the composition.

19. The method of claim 1, wherein the polyethylene glycol 400 is present in an amount of 35-50% by weight, based on the weight of the composition.

20. The method of claim 1, wherein the polyethylene glycol 400 is present in an amount of 40-50% by weight, based on the weight of the composition.

21. The method of claim 1, wherein the 2-hydroxypropyl-β-cyclodextrin has an average molecular weight of 1396 Da.

22. The method of claim 1, wherein the 2-hydroxypropyl-β-cyclodextrin has an average degree of substitution of 0.67 hydroxypropyl groups per glucopyranose unit.

23. The method of claim 1, wherein the composition comprises 2-hydroxypropyl-β-cyclodextrin.

24. The method of claim 1, wherein the DMSO is present in an amount of 5% by weight, based on the weight of the composition.

* * * * *